United States Patent
Shimada et al.

(10) Patent No.: US 8,292,806 B2
(45) Date of Patent: Oct. 23, 2012

(54) SAFETY AND HEALTH INFORMATION REPORTING SYSTEM

(75) Inventors: Kazuyuki Shimada, Saitama (JP); Hiroyuki Kuriyama, Kawasaki (JP); Mariko Yamamoto, Kokubunji (JP); Hideyuki Ban, Kodaira (JP); Manabu Furukawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 740 days.

(21) Appl. No.: 11/196,328

(22) Filed: Aug. 4, 2005

(65) Prior Publication Data

US 2006/0094938 A1 May 4, 2006

(30) Foreign Application Priority Data

Nov. 2, 2004 (JP) ................................. 2004-318671

(51) Int. Cl.
*A61B 5/00* (2006.01)
(52) U.S. Cl. ........................................ 600/301; 600/300
(58) Field of Classification Search .......... 600/300–301; 128/903–905, 920; 705/2–5
See application file for complete search history.

(56) References Cited

U.S. PATENT DOCUMENTS

| | | | | |
|---|---|---|---|---|
| 6,287,262 B1* | 9/2001 | Amano et al. | ................. | 600/500 |
| 6,475,158 B1* | 11/2002 | Orr et al. | ........................ | 600/531 |
| 6,478,736 B1* | 11/2002 | Mault | ........................... | 600/300 |
| 6,537,227 B2* | 3/2003 | Kinnunen et al. | ............ | 600/500 |
| 6,569,094 B2* | 5/2003 | Suzuki et al. | ................. | 600/300 |
| 6,605,038 B1* | 8/2003 | Teller et al. | .................. | 600/300 |
| 6,790,178 B1* | 9/2004 | Mault et al. | ................... | 600/300 |
| 7,867,141 B2* | 1/2011 | Matsumura et al. | ............. | 482/8 |
| 8,109,874 B2* | 2/2012 | Kong et al. | .................... | 600/300 |
| 2002/0165443 A1* | 11/2002 | Mori | ............................. | 600/407 |

FOREIGN PATENT DOCUMENTS

| | | |
|---|---|---|
| JP | 2003-235813 | 9/1994 |
| JP | 2002-73966 | 9/2000 |
| JP | 2002-342864 | 9/2001 |

* cited by examiner

*Primary Examiner* — Henry M Johnson, III
*Assistant Examiner* — Bobby Soriano
(74) *Attorney, Agent, or Firm* — Stites & Harbison, PLLC; Juan Carlos A. Marquez, Esq.

(57) ABSTRACT

A safety and health information reporting system including a wearable device, a metabolic index calculating part, an activity index calculating part, a safety and health status determining part and a determination result output part. The wearable device is worn by a living body. The metabolic index calculating part calculates a metabolic index which represents energy consumption of the living body, based on a detection signal of the wearable device. The activity index calculating part calculates an activity index representing an activity amount of the living body on a daily basis. The safety and health status determining part which determines a safety and health status of the living body, based on a comparison of the metabolic index and the activity index. The determination result output part outputs a determination result of the safety and health status determining part.

12 Claims, 18 Drawing Sheets

FIG.3

DATA STORAGE DATABASE 300

USER DATA HISTORY TABLE 310A

| USER ID | HS DATA | LATEST STATUS | TIME OF LATEST STATUS |
|---|---|---|---|
| ... | | | |
| user0001 | WD_ID=wd01,SD_ID=sd30,Ps=71,BT=36.0,Ac=70,LOC_BED=ON | S_ST | 2004/04/02 23:09 |
| user0001 | WD_ID=wd01,SD_ID=sd30,Ps=62,BT=35.8,Ac=10,LOC_BED=ON | S_SL | 2004/04/02 23:10 |
| ... | | | |
| user0001 | WD_ID=wd01,SD_ID=sd30,Ps=71,BT=36.0,Ac=70,LOC_BED=ON | S_ST | 2004/04/03 07:12 |
| user0001 | WD_ID=wd01,SD_ID=sd30,LOC_BED=OFF | – | 2004/04/03 07:12 |
| user0001 | WD_ID=wd01,SD_ID=td10,Ps=87,BT=36.2,Ac=107 | S_AC | 2004/04/03 07:13 |
| ... | | | |
| user0001 | WD_ID=wd01,SD_ID=td10,Ps=85,BT=36.2,Ac=90 | S_AC | 2004/04/03 23:07 |
| user0001 | WD_ID=wd01,SD_ID=sd30,BT=36.2,Ac=70,LOC_BED=ON | S_ST | 2004/04/03 23:08 |
| ... | | | |
| user0001 | WD_ID=wd01,SD_ID=sd30,Ps=62,BT=35.8,Ac=10,LOC_BED=ON | S_SL | 2004/04/03 23:12 |
| ... | | | |
| user0001 | WD_ID=wd01,SD_ID=sd30,Ps=80,BT=37.5,Ac=10,LOC_BED=ON | S_SLH_PN | 2004/04/04 23:09 |
| ... | | | |
| user0001 | Ps=50,BT=35.8,Ac=0,LOC_BED=ON | S_SLH_PE | 2004/04/05 23:10 |
| ... | | | |

311　312　313　314

REPORT HISTORY TABLE 320

| USER ID | REPORTED TIME | INTERVAL |
|---|---|---|
| ... | | |
| user0001 | 2004/04/02 23:10 | 12h |
| ... | | |

321　322　323

FIG.8
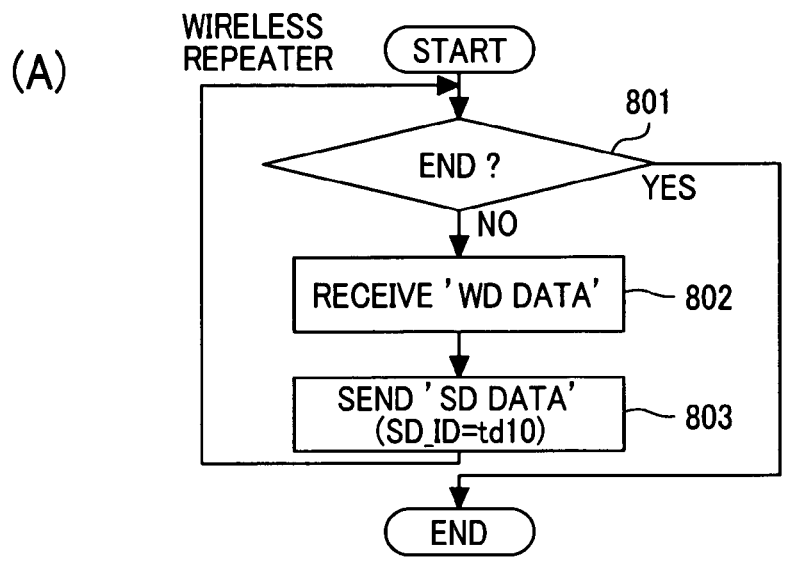
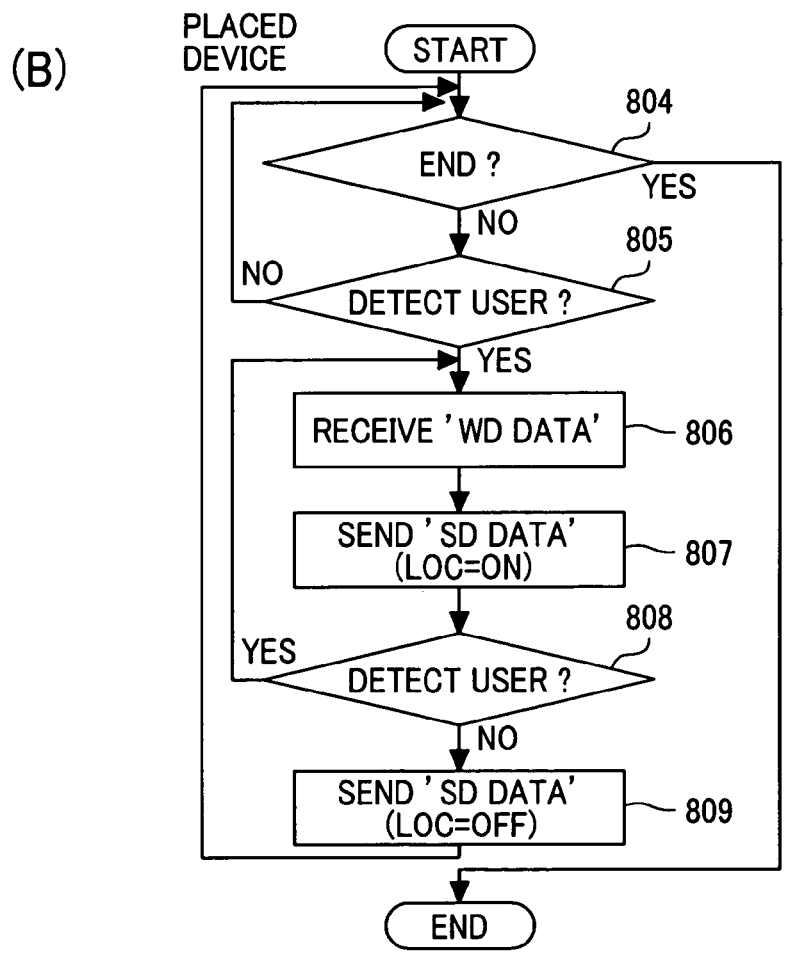

FROM : E-HEALTH
SUB : GRANDPA NOW △

----------

F.Kuri 'S STATUS
DI : ○ (2h)
SL : ○ (8h)
AC : △ (1h)
RS : ○ (5h)
HP : ○

MORE DETAIL ...

-----

MIMAMORI SUKOYAKA

1532

SAFETY AND HEALTH INFORMATION REPORTING SYSTEM

CLAIM OF PRIORITY

The present application claims priority from Japanese application JP 2004-318671 filed on Nov. 2, 2004, the content of which is hereby incorporated by reference into this application.

FIELD OF THE INVENTION

The present invention relates to a system for collecting information regarding a target resident and reporting a safety and health status (such as the status of safety, the status of health state, etc.) of the resident to particular families who watch the resident.

BACKGROUND OF THE INVENTION

In recent years, nuclear families have remarkably increased as well as decreasing children and aging families. There are many elderly (particularly over sixty years old) families consisting of a couple or living alone. There is a great demand for a watching system through which families remotely understand their parents' or grandparents' status of safety.

Conventionally, there is such a watching system that detects information regarding the resident using various domestic sensors installed inside the residence, and reports the detected information representing the status of safety.

For example, JP-A No. 73966/2002 discloses a "life monitor system" that detects and stores a user's operation or action on an electric pot, processes the stored information and sends the processed information in the form of e-mail, at intervals of a predetermined time period or in response to a request therefor.

For example, JP-A No. 342864/2002 discloses a "monitoring system" that stores history information of output signals from a human detection sensor, and sends the history information in the form of e-mail in response to a received signal of a phone.

For example, JP-A No. 235813/2003 discloses a "monitoring device" that determines the physical condition based on a judgment standard set for each user, based on detected biological information, and issues a report signal.

The conventional systems can understand whether the target resident is in a status of safety or not. However, a problem is that the conventional systems cannot understand to what extent the target resident is not safe when the resident is not in a status of safety. One particular problem is that they cannot understand whether there is a health problem or not when the resident is not in a status of safety.

SUMMARY OF THE INVENTION

It is accordingly an object of the present invention to provide an information system which reports a status of safety and a status of health of a resident, using a sensor worn by the resident and an in-house sensor.

The above-described object can be accomplished by a safety and health information reporting system including: a wearable device which includes a pulse wave sensor, a temperature sensor and a movement sensor, and which is worn by a living body; a metabolic index calculating part which calculates a metabolic index representing energy consumption of the living body, based on a detection signal of the wearable device; an activity index calculating part which calculates an index of an activity amount representing an amount of daily performance of the living body; a safety and health status determining part which determines a safety and health status of the living body, based on a comparison between the calculated metabolic index and the activity index; and a determination result output part which outputs a determination result of the safety and health status determining part.

The above-described object can be accomplished by the safety and health information reporting system, wherein the safety and health status determining part determines: a period of sleeping which is calculated based on a start time of sleeping and an end time of sleeping; a period of being active from the end time of sleeping to the start time of sleeping; a period of resting from the end time of sleeping to the start time of sleeping; a period of dining from the end time of sleeping to the start time of sleeping; and whether a heath problem is found.

The above-described object can be accomplished by a safety and health information reporting system, wherein the safety and health status determining part determines whether the living body is in a usual status or not.

The above-described object can be accomplished by a safety and health information reporting system, wherein the safety and health status determining part determines the living body is in an unusual status when the living body is not in a usual status.

The above-described object can be accomplished by a safety and health information reporting system, wherein the safety and health status determining part determines whether the living body is in a status of resting or in a status of being active.

The above-described object can be accomplished by a safety and health information reporting system, wherein the safety and health status determining part determines whether the living body is in a status of sleeping when the living body is in the status of resting.

The above-described object can be accomplished by a safety and health information reporting system, wherein the safety and health status determining part determines whether the living body is in a status of dining when the living body is in the status of being active.

The above-described object can be accomplished by a safety and health information reporting system, wherein the metabolic index calculating part calculates the metabolic index, based on an output signal of the pulse wave sensor and an output signal of the temperature sensor, while attaining the accurate calculation of the metabolic index.

The above-described object can be accomplished by a safety and health information reporting system, wherein the activity index calculating part calculates the activity index based on an output signal of the movement sensor, while attaining the simple calculation of the activity index.

The above-described object can be accomplished by a safety and health information reporting system, wherein a determination result output part outputs the determination result of the safety and health status determining part when the safety and health status determining part determines that the living body is in a status of sleeping, while improving the convenience of the service.

The above-described object can be accomplished by a safety and health information reporting system, wherein the determination result output part outputs a determination result of the safety and health status determining part in e-mail, while improving the convenience and immediateness of the service.

The above-described object can be accomplished by a safety and health information reporting system, wherein: the safety and health status determining part determines a status of safety of the living body as to whether the living body is in a usual status or not; and the determination result output part writes the status of safety of the living body in a subject of the e-mail, while improving the convenience of the service.

The above-described object can be accomplished by a safety and health information reporting system, wherein the determination result output part generates a graph including the activity index, the metabolic index and the determination result, and outputs the generated graph, while realizing simple reporting of the safety and health status in detail.

The above-described object can be accomplished by a safety and health information reporting system, further including a placed device including a human detection sensor which detects the living body, and wherein the safety and health status determining part outputs information representing a health problem of the living body, based on a detection signal of the human detection sensor, while improving the determination accuracy of the health problem.

The safety and health information reporting system, wherein the safety and health status determining part outputs e-mail representing that the health problem is determined upon determination of the health problem, while realizing the immediate reporting of the health problem.

According to the safety and health information reporting system, the families who watch the user can easily and specifically understand the status of health and safety regarding the user, thus can remotely watch the user and greatly assured of the user's status.

Because the user is aware that his/her families watch the user, the user can have a comfortable daily life without anxiety.

BRIEF DESCRIPTION OF THE DRAWINGS

FIG. 3 is a diagram showing an example of a data storage database;

FIG. 8A is a flowchart for explaining operations of a wireless repeater, and FIG. 8B is a flowchart for explaining operations of a placed device;

FIG. 15 is a diagram exemplifying a display screen shown on the user terminal at the time of displaying e-mail;

DETAILED DESCRIPTION OF THE PREFERRED EMBODIMENTS

Figure 1:
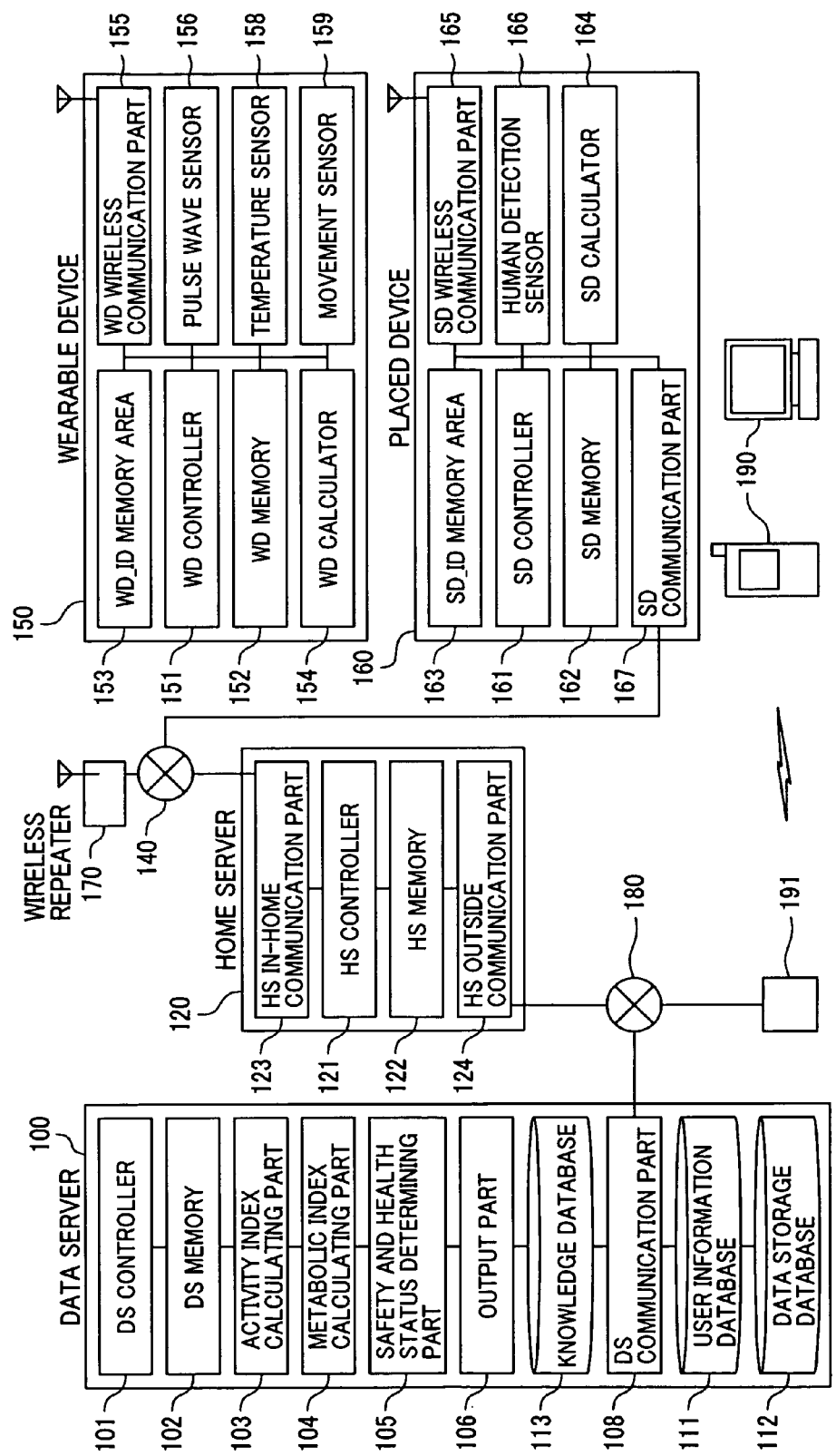
FIG. 1 is a block diagram showing a safety and health information reporting system according to an embodiment of the present invention.

FIG. 1 is a block diagram showing a safety and health information reporting system according to an embodiment of the present invention. The system includes a data server 100, a home server 120, an in-home network 140, a wearable device 150, a placed device 160, one or plural wireless repeaters 170, a network outside of home 180, a user terminal 190 and a provider 191 that relays e-mail to the user terminal 190.

When the user terminal 190 is a cellular phone, the provider 191 serves as a carrier for cellular phones. When the user terminal 190 is a personal computer for home, the provider 191 serves as an Internet Service Provider (ISP).

In this embodiment, it is assumed that the user terminal 190 is a cellular phone; however, the user terminal 190 may be a personal computer.

In the system of this embodiment, the home server 120, the placed device 160 and the wireless repeater 170 are installed in one residence within collective housing such as a condominium building. In addition, the wearable device 150 is worn by and put on the body of a resident (hereinafter referred to as a user) of the residence. The user terminal 190 is used by families (hereinafter referred to as a family user) who watch the user. The data server 100 is installed in a data center managed by a customer center (i.e. the manager of the reporting system).

Because the data server 100 is thus installed in the data center, it can unitarily manage personal information of the user and the family user, and manage also privacy information (e.g. vital data, etc.) collected from the user. This can realize simple security management, thus preventing information leakage, etc.

Alternatively, one home server 120 may be installed in a condominium building, and the placed device 160 may be installed in each residence of the condominium building. In this case, the plural the placed devices 160 are connected to one network within the condominium building, thus reducing the introduction cost of the system.

The data server 100 may be installed in the condominium building. This results in a simple configuration of the system.

In the system according to this embodiment, the home server 120, the place device 160 and the in-home network 140 may be installed in an independent house (hereinafter referred to as residence). In addition, the wearable device 150 may be worn by the resident (hereinafter referred to as a user) of the residence. In this case, the system of this embodiment can be used in independent houses.

The data server 100 includes a DS controller 101, a DS memory 102, an activity index calculating part 103, a metabolic index calculating part 104, a safety and health status determining part 105, an output part 106, a DS communication part 108, a user information database 111, a data storage database 112 and a knowledge base 113.

The home server 120 includes an HS controller 121, an HS memory 122, an HS in-home communication part 123 and an HS outside communication part 124.

The wearable device 150 includes a WD controller 151, a WD memory 152, a WD_ID memory area 153, a WD calculator 154, a WD wireless communication part 155, a pulse wave sensor 156, a temperature sensor 158 and a movement sensor 159. The WD_ID memory area 153 stores a WD_ID as a unique ID for identifying the wearable device. The pulse wave sensor 156 detects any change in blood flow inside the blood vessel, in accordance with the pulsation of the heart of a living body. The temperature sensor 158 detects the heat energy generated from the living body. The movement sensor 159 detects the movement of the target living body as body movement.

In this embodiment, the WD_ID memory area 153 stores "wd01" as an ID of the wearable device.

The wearable device 150 executes wireless communications with the wireless repeater 170 and the placed device 160.

The wearable device 150 is incorporated into a wristband, and it is assumed that the user wears the wristband on his/her wrist during its usage. However, the wearable device 150 may be incorporated into any other wearable device, such as a wrist watch, a locker key, a pendant, a ring, a cloth, a shoe, a hat, glasses, etc. The wearable device may be formed with an item, such as a sticking plaster, a wet compress, etc., so as to be directly put on the skin of the living body.

Figure 18:
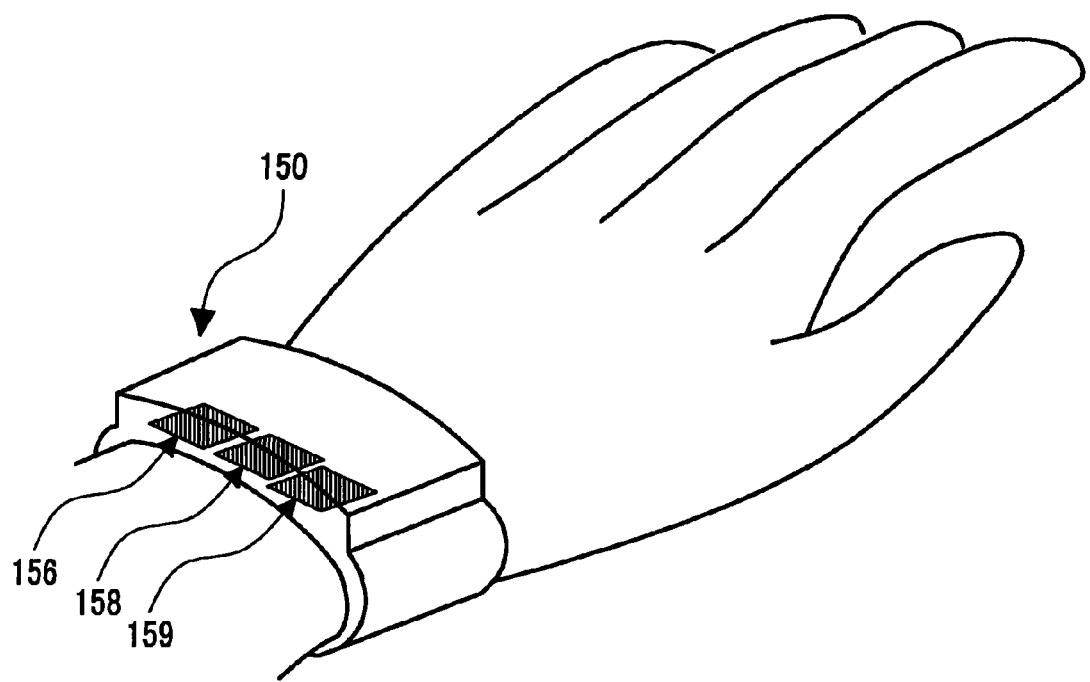
FIG. 18 is a block diagram showing the wearable device incorporated into a wristband.

FIG. 18 shows the structure of the wearable device 150 when it is incorporated into a wristband. The pulse wave sensor 156 and the temperature sensor 158 are provided near or in contact with the skin of the user. With this structure, the wearable device 150 can detect the pulse wave and temperature of the user. The movement sensor 159 is so incorporated into the wristband that it detects the user's movement in a direction parallel to the back of his/her hand. With this structure, the wearable device 150 can efficiently detect the user's movement and actions.

The movement sensor 159 may be an impact sensor, thus reducing the power consumption. The movement sensor 159 may be an acceleration sensor, thus detecting the movement of the user with high accuracy.

The placed device 160 includes an SD controller 161, an SD memory 162, an SD_ID memory area 163, an SD calculator 164, an SD wireless communication part 165, a human detection sensor 166 and an SD communication part 167. The SD_ID memory area 163 stores an SD_ID as a unique ID for identifying the placed device.

In this embodiment, the SD_ID memory area 163 stores "sd01" as an ID of the placed device.

It is assumed that the human detection sensor 166 is a piezoelectric sensor whose output voltage changes upon detection of the pressure. However, the human detection sensor 166 may be any other sensor, for example, a pyroelectric infrared sensor whose output voltage changes upon detection of the heat energy generated from the living body. The human detection sensor 166 may be formed in combination with the piezoelectric sensor, the pyroelectric infrared sensor, and/or another sensor.

The in-home network 140 is connected to the home server 120, the place device 160 and the wireless repeater 170. The home server 120 executes communications with the placed device 160 and the wireless repeater 170 through the in-home network 140.

It is assumed that the in-home network 140 is wire communications network using a LAN (Local Area Network) cable. However, the in-home network 140 may be a PLC (Power Line Communication) system, another wire communications network, a wireless communications network (e.g. IEEE802.11b, etc.), or any other original communication system.

It is assumed that the placed device 160 is provided in some furniture, such as a bed or the like. However, the placed device 160 may be provided in other furniture, home electric appliances or household facilities, such as a sofa, a massage chair, a desk chair, a floor, etc. on which the user can be secured to maintain a status of resting within the residence.

Figure 19:
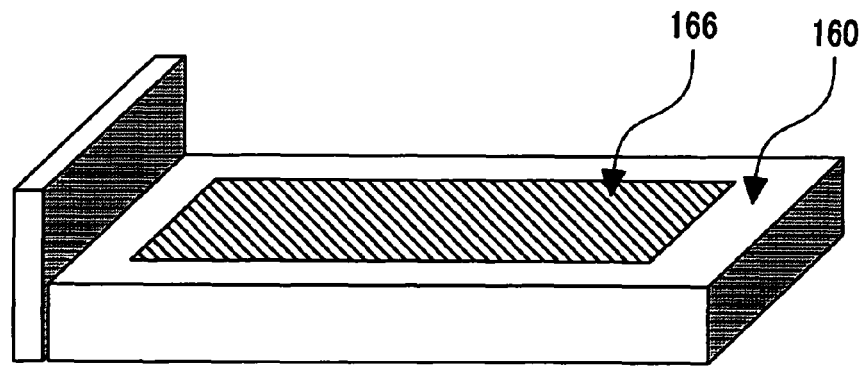
FIG. 19 is a block diagram showing the placed device installed in a bed.

FIG. 19 is a block diagram showing the placed device 160 installed in a bed. The human detection sensor 166 is provided in contact with the user, thus enabling to detect the user.

The system according to this embodiment has so far been described from its hardware aspect; however, the system may partially include software.

Figure 2:
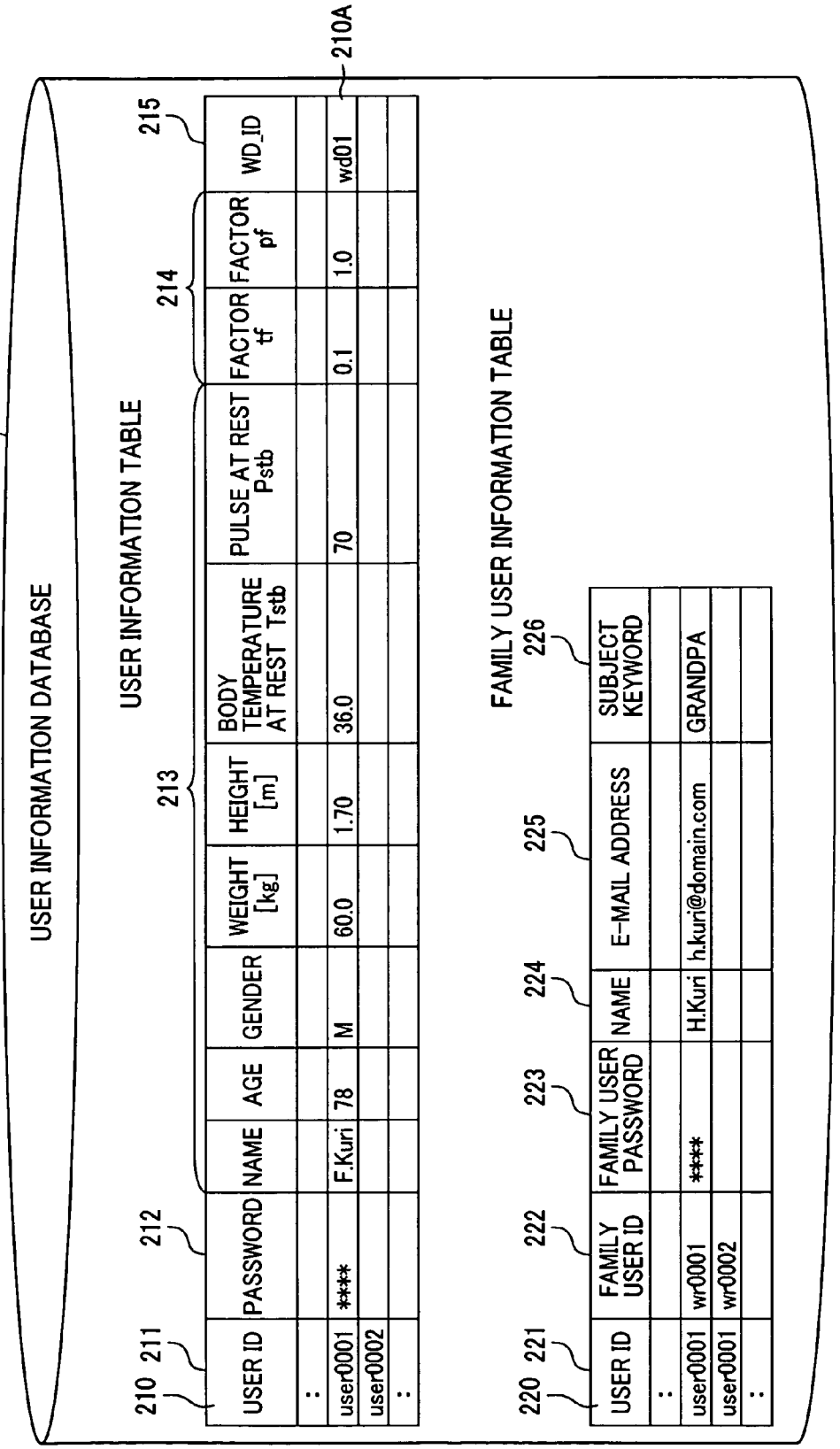
FIG. 2 is a diagram showing an example of a user information database.

FIG. 2 shows an example 200 of the user information database 111. The database example 200 includes a user information table 210 and a family user information table 220. The table 210 manages personal information of users, while the table 220 manages information of family users. The user information table 210 is composed of fields 211, 212, 213, 214 and 215. The field 211 stores user "ID" for identifying the users. The field 212 stores user "password" necessary for authenticating the users when they intend to use the system. The field 213 stores personal information, including each user's "name", "age", "gender", "weight", "height", "body temperature at rest" (Tstb), and "pulse at rest" (Pstb). The field 214 stores "temperature factor" (tf) and "pulse factor" (pf). The field 215 stores "WD_ID" for identifying the wearable device used by each user. For example, as shown in the table example 210, a user corresponding to the user ID "user 0001" and the user name "F. Kuri" is "78" years old, "male", weight "60" kg, "1.7" meter in height, has a body temperature at rest (Tstb) of "36.0" ° C. and pulse at rest (Pstb) of "70"/min., and uses a wearable device identified by a WD_ID "wd01". In addition, the temperature factor (tf) is "0.1", while the pulse factor (pf) is 1.0.

The family user information table 220 is composed of fields 221, 222, 223, 224, 225 and 226. The field 221 stores user "ID" for identifying the users. The field 222 stores family user "ID" for identifying the family users. The field 223 stores family user "password" necessary for authenticating the family users when they intend to use the system. The field 224 stores family user "name". The field stores 225 stores family user's "e-mail address" to which the safety and health status of a corresponding user is reported in e-mail. The field 226 stores "subject keyword" written in the subject of the reporting e-mail.

For example, as shown in the table example 220, a family user identified by the family user ID "wr0001" and corresponding to the user name "H. Kuri" is registered to receive e-mail having a subject with a subject keyword of "GRANDPA". This e-mail is to report the safety and health status of the user "user0001", and addressed to "h.kuri@domain.com".

The e-mail address stored in the field 225 and the subject keyword stored in the field 226 can be set, as the family user likes, after the user authentication.

FIG. 3 shows an example 300 of the data storage database 112. The data storage database 112 is composed of a user data history table 310 and a report history table 320. The user data history table 310 is composed of fields 311, 312, 313 and 314. The field 311 stores the user IDs. The field 312 stores HS data including vital data of the user that is sent from the home server 120. The field 313 stores the safety and health status obtained based on the vital data of the user. The field 314 stores the latest time the HS data is received.

The report history table 320 is composed of fields 321, 322 and 323. The field 321 stores the user IDs. The field 322 stores the latest reported time. The field 323 stores the interval between reporting times.

The table 320 explains that the system has reported the safety and health status of the user ID "user0001" at the reported time of "2004/04/02 23:10", and will again report the safety and health status of the user twelve hours after the latest reported time, i.e. at or after "2004/04/03 11:10".

Figure 4:
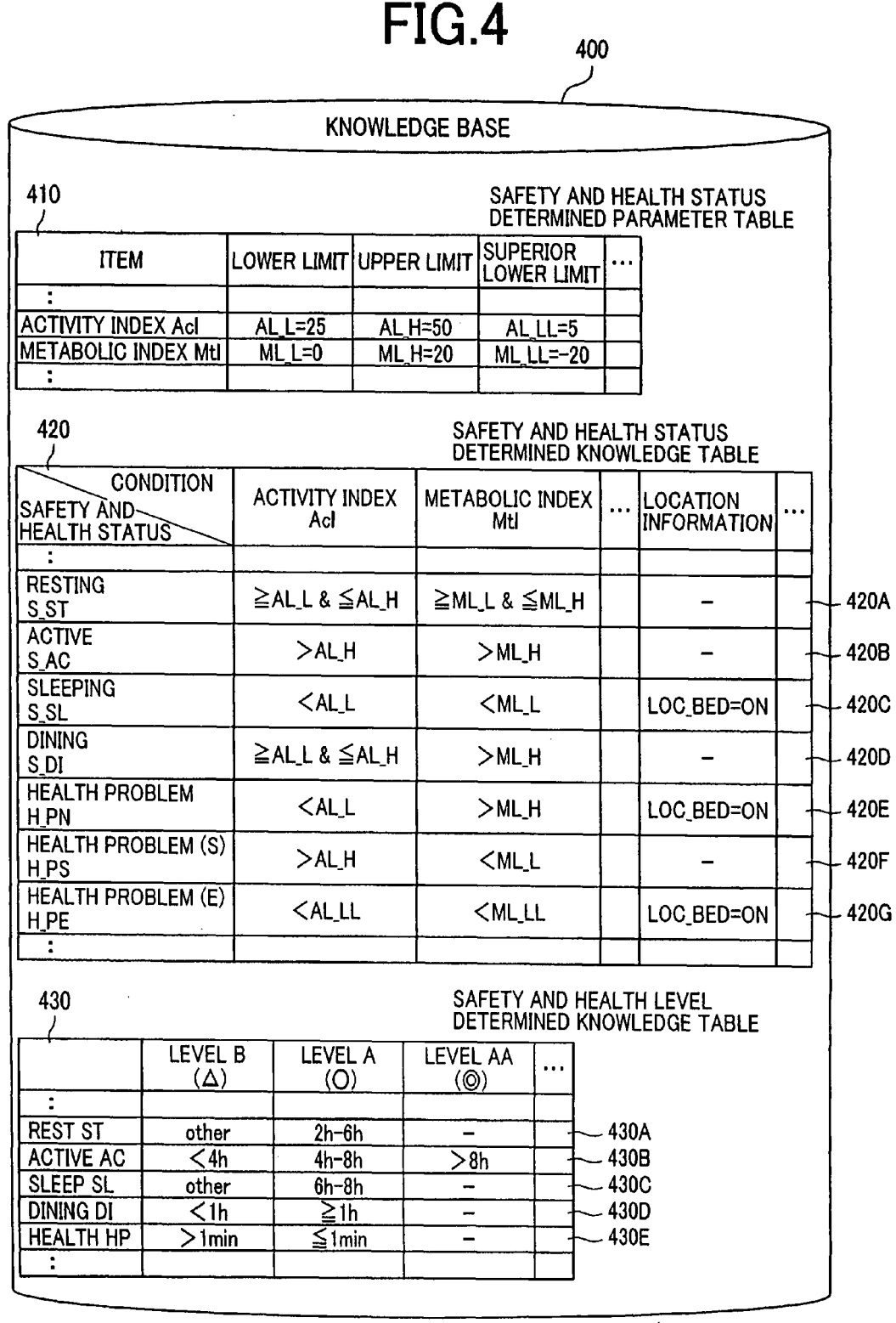
FIG. 4 is a diagram showing an example of a knowledge database.

FIG. 4 shows an example 400 of the knowledge base 113. The knowledge base 113 includes a safety and health status determined parameter table 410, a safety and health status determined knowledge table 420 and a safety and health status level determined knowledge table 430. The safety and health status determined parameter table 410 stores "lower limit AcI_L", "upper limit ACI_H" and "superior lower limit AcI_LL" of "activity index AcI". The table 410 also stores "lower limit MtI_L", "upper limit MtI_H" and "superior lower limit MtI_LL" of "metabolic index MtI". These indexes are necessary for determining the safety and health status of the user.

The safety and health status determined knowledge table 420 stores conditions for determining the safety and health status regarding the status of health and the health problem, at a predetermined time. As seen from the table 420, for example, when determining one health status "resting" (S_ST), this determination is made based on a condition 420A of "when the activity index AcI is equal to or greater than the lower limit AcI_L and equal to or smaller than the upper limit AcI_H, while the metabolic index MtI is equal to or greater than the lower limit MtI_L and equal to or smaller than the upper limit MtI_H". In addition, when determining one health status "being active" (S_AC), this determination is made based on a condition 420B of "when the activity index AcI is greater than the upper limit AcI_H". When determining one health status "sleeping" (S_SL), this determination is made based on a condition 420C of "when the activity index AcI is smaller than the lower limit AcI_L". For example, when determining one health status "dining" (S_DI), this determination is made based on a condition 420D of "when the activity index AcI is equal to or greater than the lower limit AcI_L and equal to or smaller than the upper limit AcI_H, while the metabolic index MtI is greater than the upper limit MtI_H".

When determining one health status "health problem" (H_PN), this determination is made based on a condition 420E of "when the activity index AcI is smaller than the lower limit AcI_L, while the metabolic index MtI is greater than the upper limit MtI_H". For example, when determining one health status "health problem" (H_PS), this determination is made based on a condition 420F of "when the activity index AcI is greater than the upper limit AcI_H, while the metabolic index MtI is smaller than the lower limit MtI_L". When determining one health status "health problem in emergency" (H_PE), this determination is made based on a condition 420G of "when the activity index AcI is smaller than the superior lower limit AcI_LL, while the metabolic index MtI is smaller than the superior lower limit MtI_LL".

The safety and health status level determined knowledge table 430 stores conditions for determining the level of the safety and health status on a daily basis. For example, when determining the level of the safety and health status "active" (AC), this determination is made based on a condition 430B such as when the total time ACT of "active" (S_AC) is in a range between four hours and less than eight hours, level A (expressed by circle) is given, when the total time of "active" is less than four hours, level B (expressed by triangle) is given, and when the total time of "active" is greater than eight hours, level AA (expressed by double circle) is given. When determining the level of the safety and health status "health HP", this determination is made based on a condition 430E such as when the total time HPT of "health problem" (H_PN), "health problem(s)" (H_PS) and "health problem in emergency" (H_PE) is equal to or less than one minute, level A (expressed by circle) is given, and when the total time HPT is greater than one minute, level B (expressed by triangle) is given".

Figure 5:
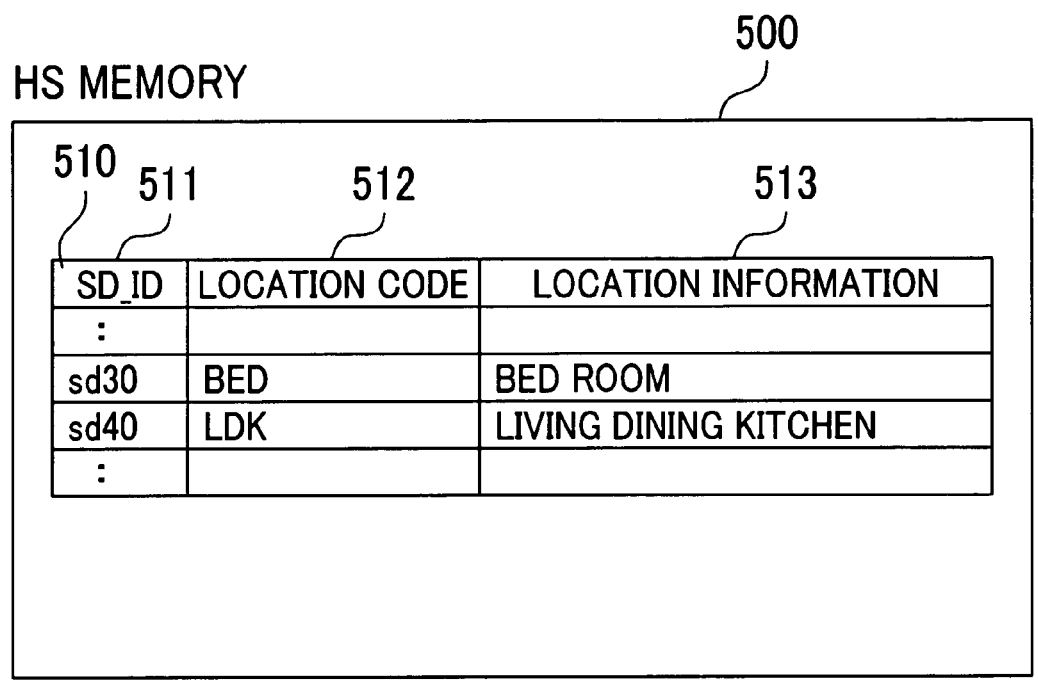
FIG. 5 is a diagram showing an example of an HS memory.

FIG. 5 shows an example 500 of the HS memory 122. The HS memory 122 includes a table 510 storing information regarding the placed device. The table 510 is composed of fields 511, 512 and 513. The field 511 stores the "SD_ID", the field 512 stores the "location code" for identifying the location of the user, and the field 513 stores "location information". As seen from the example 500, the placed device identified by the SD_ID "sd30" is provided in a bedroom identified by a location code "BED". Similarly, the placed device identified by the SD_ID "sd40" is provided in the living-dining kitchen identified by a location code "LDK".

Figure 6:
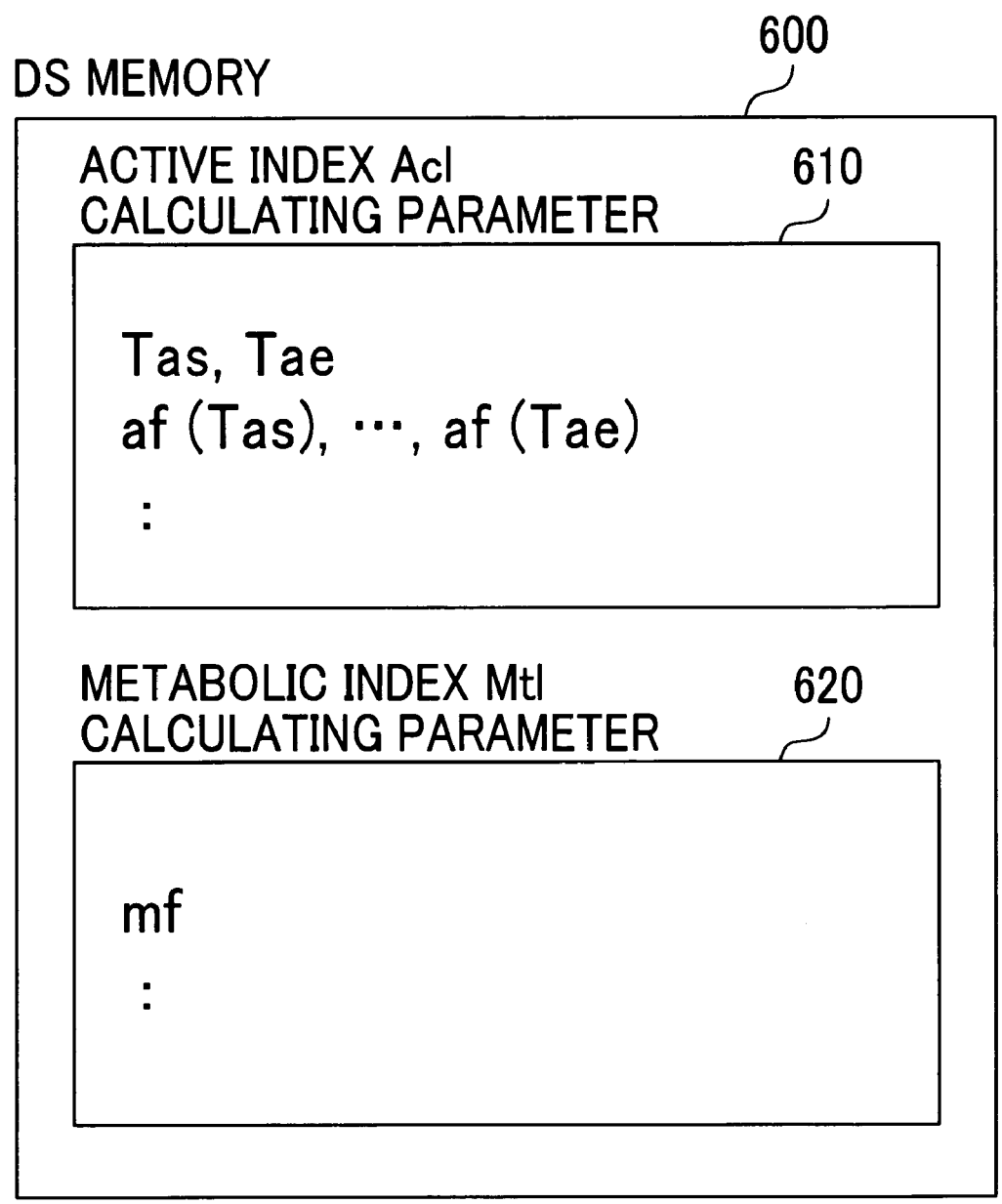
FIG. 6 is a diagram showing an example of a DS memory.

FIG. 6 shows an example 600 of the DS memory 102. The DS memory 102 includes Activity Index calculating parameters 610 and Metabolic Index calculating parameters 620.

In this embodiment, one set of parameters 610 and parameters 620 are stored in the DS memory 102. However, the parameters 610 and 620 may be stored for each user. In this case, the activity index AcI and the metabolic index MtI can be obtained in accordance with the behavioral and physical characteristics of each user.

Figure 7:
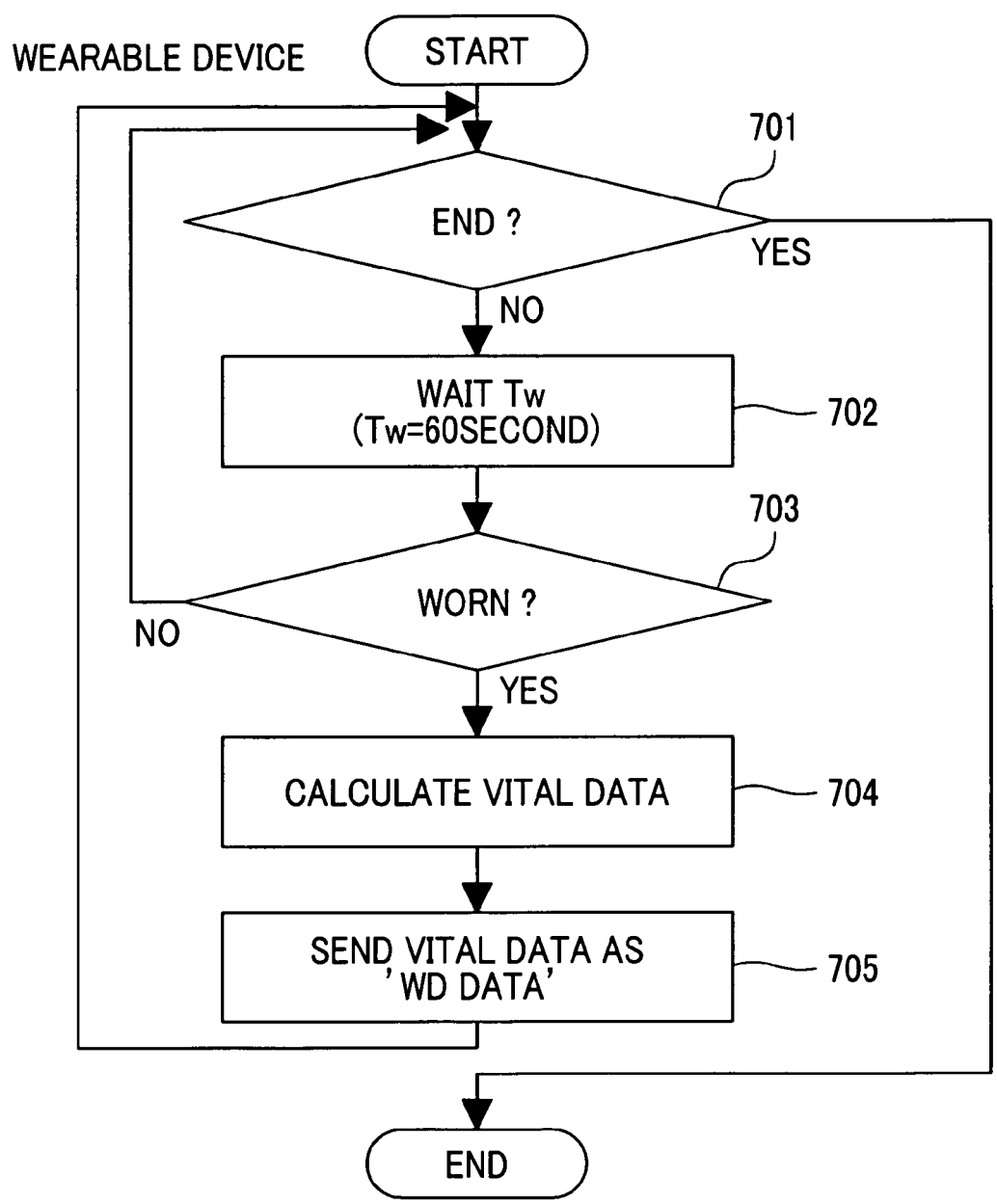
FIG. 7 is a flowchart for explaining operations of a wearable device.

Operations of the system according to this embodiment will now be depicted using a flowchart of FIG. 7.

FIG. 7 is a flowchart for explaining operations of the wearable device 150. When the wearable device 150 starts an operation, the WD controller 151 carries out a step 701 to determine whether to end this operation. In the step 701, if it is determined to end the operation, the WD controller 151 ends the operation.

In the step 701, if the WD controller 151 determines not to end this operation, it executes a step 702 to wait for a waiting time Tw. In this embodiment, the waiting time Tw is set to "60 seconds"; however, it may arbitrarily be set to any other period of time.

The WD controller 151 executes a step 703 to determine whether the user wears the wearable device 150. The WD controller 151 determines that the user is wearing the wearable device 150, for example, if an output value of the pulse wave sensor 156 is lower than a predetermined value, and that the user is not wearing the wearable device if the output value is equal to or greater than the predetermined value.

If the WD controller 151 determines that the user is not wearing the wearable device in the step 703, it executes the step 701, and repeats the following operations.

If the WD controller 151 determines in the step 703 that the user is wearing the wearable device, it activates the WD calculator 154 in order to execute a step 704 to obtain the pulse frequency Ps from the pulse wave sensor 156, the body temperature BT from the temperature sensor 158, the body movement Ac from the movement sensor 159, so as to calculate vital data of the user.

For example, when obtaining the pulse frequency Ps, the WD calculator 154 obtains the peak value of the pulse wave output by the pulse wave sensor 156, and counts the number of peak values during the last sixty seconds, thereby obtaining the counted result as the pulse frequency Ps.

For example, when obtaining the body temperature BT, the WD calculator 154 obtains the temperature BT using a transformation for transforming a voltage value into a temperature, based on the voltage value output by the temperature sensor 158.

For example, when obtaining the body movement Ac, the WD calculator 154 obtains the number of times a scalar value corresponding to the degree of the body movement which is output by the movement sensor 159 shifts from a value equal to or lower than a predetermined value to a value greater than the predetermined value, obtains also the number of times the scalar value shifts from a value greater than the predetermined value to a value equal to or lower than the predetermined value, adds the obtained numbers of times together, and obtains the sum of the addition as the body movement Ac.

The WD controller 151 activates the WD wireless communication part 155 in order to execute a step 705 to send, as WD data, the vital data obtained in the step 704 together with the WD_ID.

For example, if the vital data includes the pulse frequency Ps "80", the temperature BT "36.2" and the body movement Ac "70", the WD wireless communication part 155 sends the WD data (WDDATA01) including "WD_ID=wd01, Ps=80, BT=36.2, Ac=70".

The WD data sent in the step 705 is received by the wireless repeater 170 or the placed device.

FIG. 8A shows a flowchart for explaining operations of the wireless repeater 170, when the wireless repeater 170 receives the WD data.

When the wireless repeater 170 starts an operation, the wireless repeater 170 executes a step 801 to determine whether to end this operation. If it is determined to end the operation in the step 801, the wireless repeater 170 ends this operation.

If the wireless repeater 170 determines not to end this operation in the step 801, it executes a step 802 to receive the WD data sent by the placed device 150.

The wireless repeater 170 executes a step 803 to add an SD_ID (SD_ID "td10" in this embodiment) for identifying the wireless repeater 170 to the received WD data and send resultant data as SD data.

For example, if the wireless repeater 170 has received the WDDATA01, it sends SD data (SDDATA01) representing "WD_ID=wd01, SD_ID=td10, Ps=80, BT=36.2, AC=70".

In this embodiment, it is assumed that weak radio is applied for wireless communications between the WD wireless communication part 155 of the wearable device 150 and the wireless repeater 170 and between the WD wireless communication part 155 of the wearable device 150 and the SD wireless communication part 165 of the placed device 160. Due to the weak radio communications, the power consumption can be reduced. Only when the user wearing the wearable device approaches the placed device, the placed device can receive the WD_ID sent by the wearable device, thus simplifying the identifying of the user.

Such radio communications may be any other form of radio communications, such as Zigbee, specific lower power radio, Bluetooth, IEEE802.11b, etc. Hence, a general-purpose system can be configured.

FIG. 8B shows a flowchart for explaining operations of the placed device 160. When the placed device 160 starts an operation, the SD controller 161 executes a step 804 to determine whether to end this operation. If the placed device 160 determines in the step 804 to end this operation, it ends the operation.

In the step 804, if the placed device 160 determines not to end this operation, the SD controller 161 executes a step 805 to determine whether the human detection sensor 166 detects the user.

In the step 805, if the SD controller 161 determines that the human detection sensor 166 has not detected the user, the controller 161 executes the step 804, and repeats the following operation(s).

In the step 805, if the SD controller 161 determines that the human detection sensor 166 has detected the user, the SD controller 161 executes a step 806 to receive the WD data sent by the wearable device 150. At this time, the SD controller 161 extracts a WD_ID from the received WD data, and stores the extracted ID in the SD memory.

The SD controller 161 executes a step 807 to send, as SD data, detection information (LOC=ON) representing the status that the user has been detected, together with the received WD data and SD_ID.

For example, in the case where the WDDATA01 is received, the SD controller 161 sends the SD data (SDDATA02) representing "WD_ID=wd01, SD_ID=sd30, Ps=80, BT=36.2, Ac=70, LOC=ON".

The SD controller 161 executes a step 808 to determine whether the user has been detected, like the step 805.

In the step 808, if the SD controller 161 determines that the user has been detected, it executes the step 806, and repeats the following operations.

In the step 808, if the SD controller 161 determines that the user has not been detected, the SD controller 161 executes a step 809 to send, as SD data, detection information (LOC=OFF) representing the status that the user has not been detected, together with the WD_ID stored in the SD memory.

In this case, the SD (SDDATA03) to be sent represents "WD_ID=wd01, SD_ID=sd30, LOC=OFF".

In the step 809, upon transmission of the SD data, the WD_ID stored in the SD memory is deleted.

The SD data sent in the steps 807 and 809 is received by the home server 120 through the in-home network 140.

Figure 9:
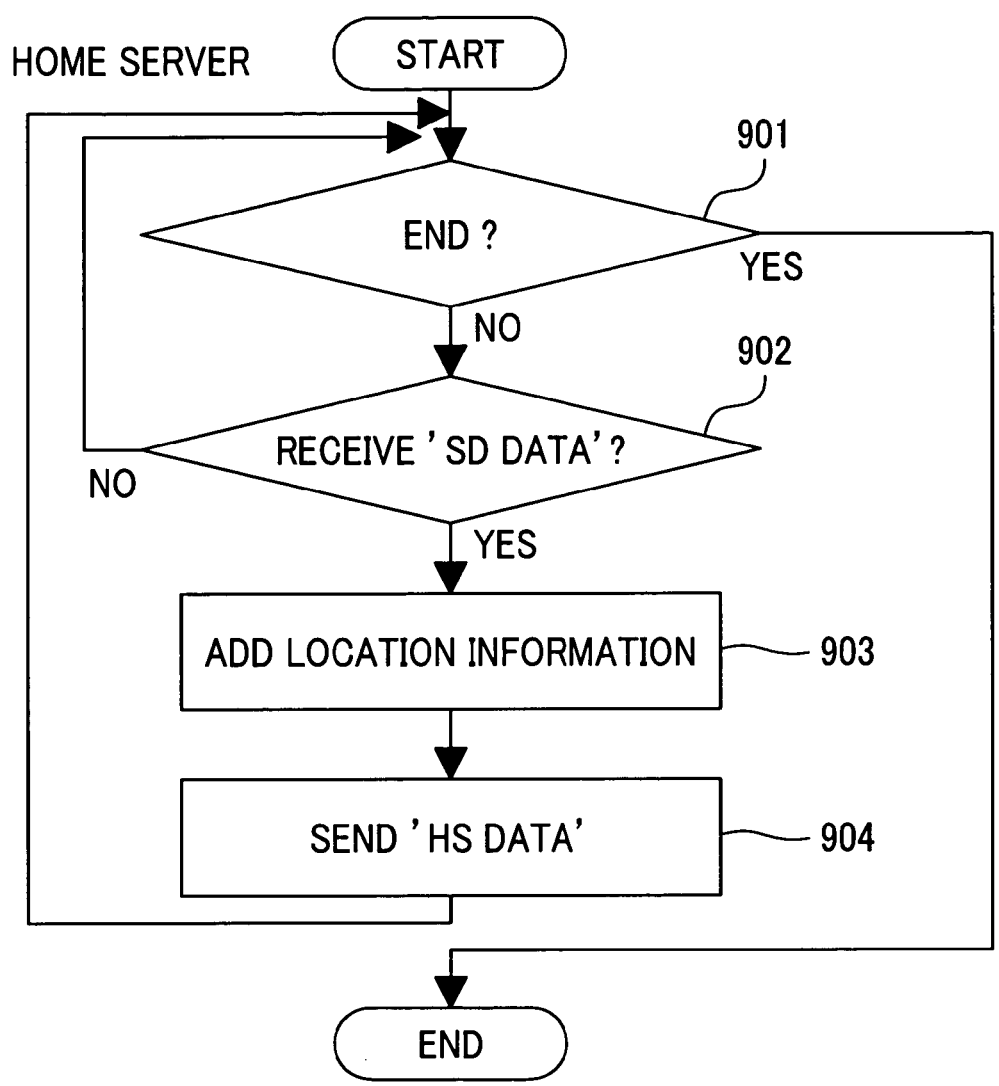
FIG. 9 is a flowchart for explaining operations of a home server.

FIG. 9 shows a flowchart for explaining operations of the home server 120. When the home server 120 starts the operation, the HS controller 121 executes a step 901 to determine whether to end this operation. In the step 901, if it is determined to end this operation, the HS controller 121 ends the operation.

In the step 901, if the HS controller 121 determines not to end this operation, it executes a step 902 to receive the SD data from the wireless repeater 170 or the SD data from the placed device 160.

The HS controller 121 executes a step 903 to generate location information together with the received SD data. For example, if the SD data includes the SD_ID "sd30" and the detection information "LOC=ON", the HS controller 121 extracts a record 510A stored in the HS memory 500, and generates the location information representing "LOC_BED=ON".

The HS controller 121 executes a step 904 to send, as HS data, the SD data received in the step 902 together with the location information generated in the step 903.

For example, if the SD data (SDDATA02) is received, the HS controller 121 sends data representing "WD_ID=wd01, SD_ID=sd30, Ps=80, BT=36.2, Ac=70, LOC_BED=ON" (HSDATA02), as HS data.

For example, if the SD data (SDDATA03) is received, the HS controller 121 sends data representing "WD_ID=wd01, SD_ID=sd30, LOC_BED=OFF", as HS data.

The HS data sent in the step 904 is received by the data server 100 through the network outside of home 180.

Figure 10:
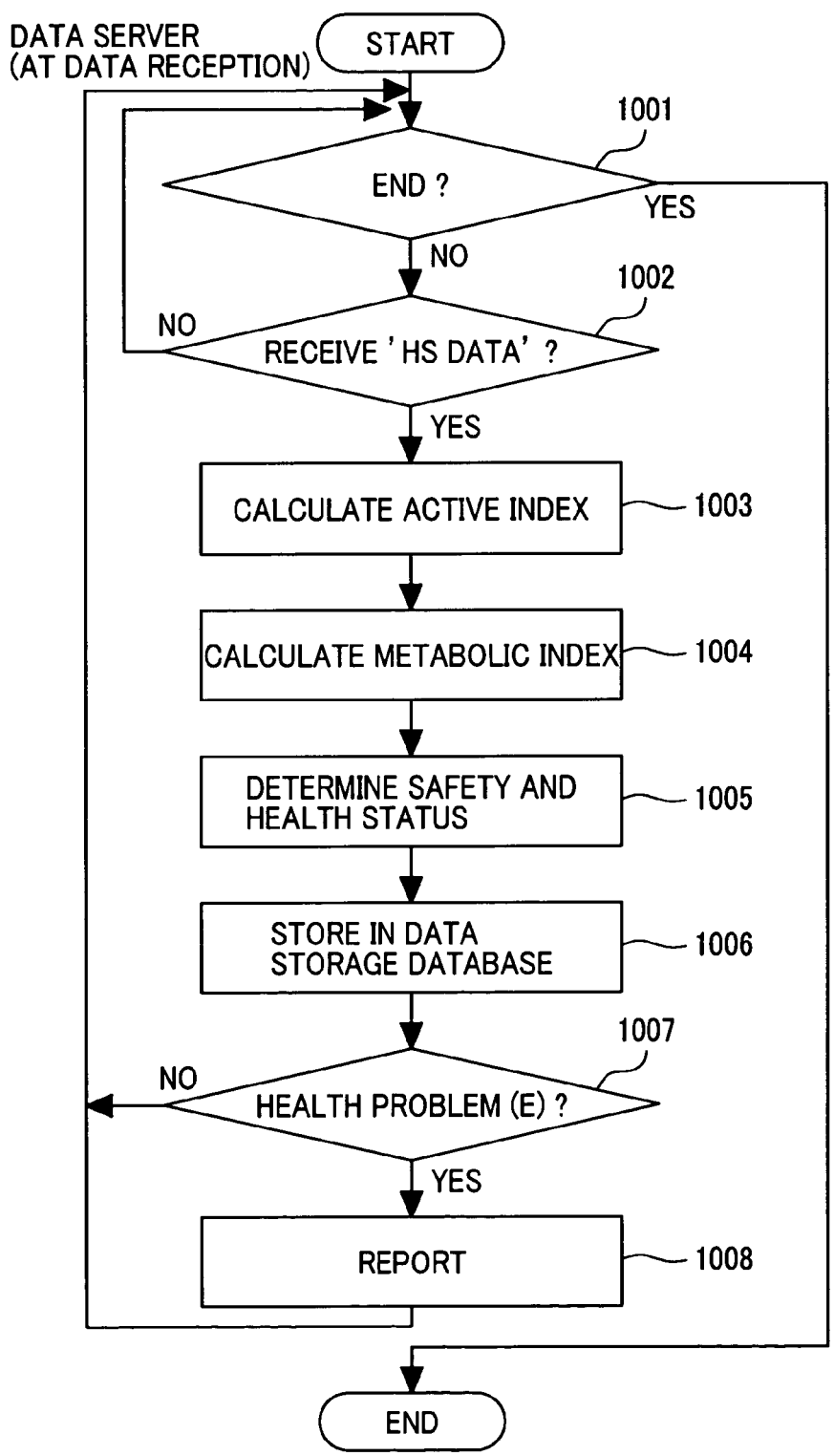
FIG. 10 is a flowchart for explaining operations of a data server at data reception.

FIG. 10 shows a flowchart for explaining operations of the data server 100 at data reception. When the data server starts an operation, the DS controller 101 executes a step 1001 to determine whether to end this operation at data reception. In the step 1001, if the DS controller determines to end this operation, this operation is ended.

In the step 1001, if the DS controller determines not to end this operation, the DS controller 101 executes a step 1002 to receive the HS data sent from the home server 120.

The DS controller 101 activates the activity index calculating part 103, and executes a step 1003 to calculate an activity index representing the characteristic of the activity amount representing an amount of daily performance of the living body. This activity index is obtained based on the HS data received in the step 1002 and the activity index calculating parameter 610 stored in the HS memory.

In this embodiment, in the step 1003, the activity index calculating part 103 obtains the activity index AcI at a predetermined time t, using the following equation.

$$AcI(t) = \sum_{i=t+Tas}^{t+Tae} \{af(i-t) \times Ac(i)\}/1000$$

where t: predetermined time [min]
Tas, Tae: starting time and ending time for setting the range of an Ac value
af (x): coefficient regarding a time lag "x" for predetermined time t
Ac (i): Ac value at time i
AcI (t): activity index of predetermined time t (the figures below the decimal point to be omitted).

For example, the parameters 610 include: Tas=−4, Tae=0, af (−4)=106, af(−3)=54, af (−2)=58, af(−1)=76, and af(0)=230. When Ac(T−4)=111, Ac(T−3)=105, Ac(T−2)=106 and Ac(T−1)=90, if the HSDATA02 is received at time T, Ac(T)=70. Therefore, the activity index AcI at time T is "46".

The DS controller 101 activates the metabolic index calculating part 104, and executes a step 1004 to calculate a metabolic index representing the characteristic of the metabolism of the living body (i.e. the energy consumption). In this case, the metabolic index is obtained based on the HS data received in the step 1002, the Metabolic Index calculating parameter 620, and the data stored in the user information table 210.

In this embodiment, in the step 1004, the metabolic index calculating part 104 calculates the metabolic index MtI at a predetermined time t, using the following equation.

$$MtI(t) = mf \times [tf \times \{BT(t) - Tstb\} + pf \times \{Ps(t) - Pstb\}/\{(220 - AGE) - Pstb\}]$$

where
t: predetermined time [min]
mf: adjustment coefficient
tf: temperature–metabolism conversion coefficient
pf: pulse–metabolism conversion coefficient
Tstb: body temperature at rest
Pstb: pulse at rest
AGE: age
MtI (t): metabolic index at predetermined time t (the figures below the decimal point to be omitted).

For example, if the set parameters 620 include mf=100, if the HSDATA02 is received at time T, BT(T)=36.2, Ps(t)=80. Therefore, the metabolic index MtI at the predetermined time T is "14".

In this embodiment, the metabolic index calculating part relatively obtains the metabolic index representing the metabolic characteristic of the living body (i.e. the energy consumption), with reference to the energy consumption at rest. However, the metabolic index may be obtained based on the absolute metabolism. In such a case, the metabolic index at the predetermined time t is obtained using the following equation, for example.

$$MtI(t) = mf \times [tf \times BT(t) + pf \times \{Ps(t) - Pstb\}/\{(220 - AGE) - Pstb\}]$$

As a result, the relation between the metabolic index and the metabolism can be clarified.

The DS controller 101 activates the safety and health status determining part 105 in order to execute a step 1005 to determine the safety and health status regarding the health status and any health problem of the user. In this case, the determination is carried out using a knowledge base stored in the safety and health status determined knowledge table 420, based on the activity index AcI calculated in the step 1003 and the metabolic index MtI calculated in the step 1004.

For example, if the HSDATA02 is received, the activity index AcI is "46" and the metabolic index MtI is "14". Thus, the safety and health status is "resting" (S_ST).

For example, if the activity index AcI is "60" and the metabolic index MtI is "30", it is clear that a large activity amount and a high level of metabolism are obtained. Thus, the safety and health status is "being active" (S_AC).

For example, if the activity index AcI is "10" and the metabolic index MtI is "−5", it is clear that a small activity amount and a low level of metabolism are obtained. Thus, the safety and health status is "sleeping" (S_SL).

For example, if the activity index AcI is "40" and the metabolic index MtI is "22", the activity amount is approximately equal to that in the "sleeping" (S_SL) and a high level of metabolism is obtained. Thus, the safety and health status is "dining" (S_DI).

For example, if the activity index AcI is "10" and the metabolic index MtI is "30", a small activity amount and a high level of metabolism are obtained. In this case, a health problem is suspected from some cause, such as infections or stresses. Thus, the safety and health status is "health problem H_PN".

For example, if the activity index AcI is "54" and the metabolic index MtI is "−2", a large activity amount is obtained, although a low level of metabolism is obtained. In this case, a health problem is suspected from some cause, such as fatigue or loss of concentration. Thus, the safety and health status is "health problem(s)" (H_PS).

For example, if the activity index AcI is "0" and the metabolic index MtI is "−10", a small activity amount and a remarkably low level of metabolism are obtained. In this case, a serious health problem is suspected. Thus, the safety and health status is "health problem in emergency" (H_PE).

As described above, by comparing the obtained the activity index representing the characteristic of the activity amount with the metabolic index representing the characteristic of the metabolism, it is possible to determine each of those fundamental factors (resting, being active, sleeping and dining) of the health status and the safety and health status regarding the health problem.

In other words, if the determining part tries to determine the safety and health status of the user based only on the metabolic index MtI, it cannot distinguish whether the level of metabolism is high because of some normal daily factor such as "being active", "dining", etc. or because of some health problem such as infections or stresses. However, the determining part compares the metabolic index MtI and the activity index AcI, thereby enabling to understand the reason why the level of the metabolism is high.

If the metabolism is low, the determining part cannot discriminate whether the metabolism is low because of some normal daily factor (such as "sleeping") or because of some health problem (such as infections or stresses). However, the determining part compares the metabolic index MtI with the activity index AcI, thereby enabling to understand the reason why the metabolism is low.

In this manner, by calculating the activity index representing the characteristic of the activity amount and the metabolic index representing the characteristic of the metabolism and comparing the calculated indexes, the safety and health status regarding the health problem can accurately be determined.

The DS controller 101 executes a step 1006 to store, in the data storage database 112, the HS data received in the step 1002 and the safety and health status obtained in the step 1005, together with information representing the time this HS data is received and also a corresponding user ID. This user ID is stored in a record corresponding to the WD_ID of the HS Data which corresponds to the WD_ID field 215 of the user information table 210.

For example, if the HSDATA02 is received at 23:08, Apr. 3, 2004, a record 310A is stored in the user data history table 310.

In this manner, the received HS data is all stored in the user data history table 310, with information representing the received time.

Figure 11:
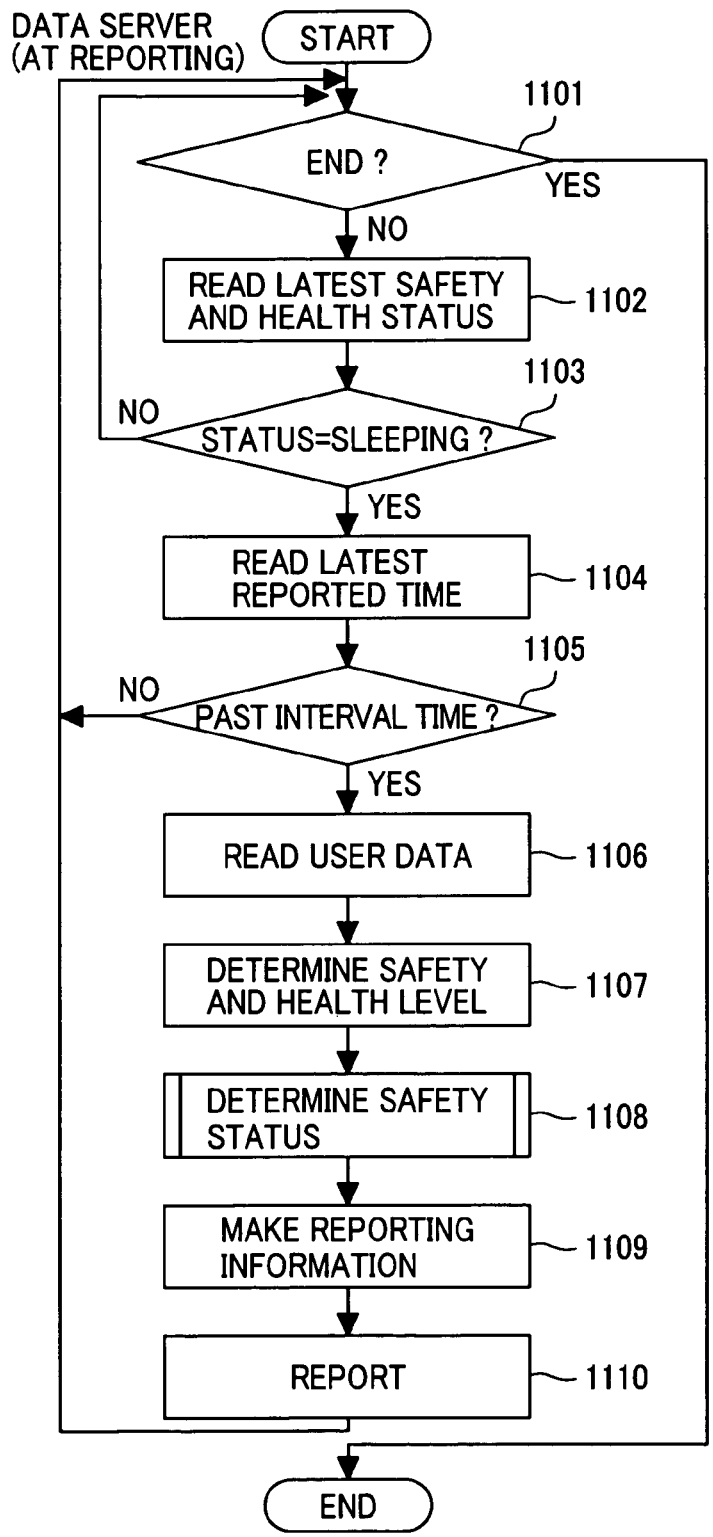
FIG. 11 is a flowchart for explaining operations of the data server at the time of reporting information.

FIG. 11 shows a flowchart for explaining operations of the data server 100 at the time of reporting. When the data server 100 starts an operation, the DS controller 101 executes a step 1101 to determine whether to end this operation at the time of reporting. In the step 1101, if the DS controller 101 determines to end this operation, the operation is ended.

In the step 1101, if the DS controller 101 determines not to end this operation, it searches the user data history table 310 of the data storage database 112, and executes a step 1102 to extract the latest safety and health status therefrom.

The DS controller 101 executes a step 1103 to determine whether the safety and health status extracted in the step 1102 is "S_SL" representing that the user "sleeping".

In the step 1103, if the DS controller 101 determines that the status is not "S_SL", it executes the step 1101, and repeats the following operations.

In the step 1103, if it is determined that the status is "S_SL", the DS controller 101 searches the report history table 320 of the data storage database 112, and executes a step 1104 to extract the latest reported time and the interval time and stores the extracted information in the DS memory 102.

The DS controller 101 compares the present time with the latest reported time stored in the DS memory 102, and executes a step 1105 to determine whether the interval time has elapsed or not.

In the step 1104, if it is determined that the interval time has not elapsed yet, the DS controller 101 executes the step 1101 and repeats the following operations.

In the step 1104, if it is determined that the interval time has elapsed, the DS controller 101 searches the user data history table 310 of the data storage database 112, and executes a step 1106 to extract corresponding user data whose interval time has elapsed since the latest reported time stored in the DS memory 102 and to store the extracted data in the DS memory 102.

The DS controller 101 activates the safety and health status determining part 105, and executes a step 1107 to determine the level of the safety and health status using the knowledge base stored in the safety and health status level determined knowledge table 430 of the knowledge base 113, based on the user data stored in the DS memory 102.

For example, if the safety and health status is "resting" (S_ST) totally for 120 minutes (=2 hours), the level A (circle) is given for this status "resting" (ST). If the safety and healthy status is "being active" (S_AC) totally for 240 minutes (=4 hours), the level AA (double circle)) is given. If the safety and health status is "sleeping" (S_SL) totally for 480 minutes (=8 hours), the level A is given (circle) for this status "sleeping". If the safety and health status is "dining" (S_DI) totally for 120 minutes (=2 hours), the level A (circle) is given for this status "dining DI". If the safety and health status of "health problem" (H_PN), "health problem(s) H_PS" and "health problem(e) H_PE" is determined totally 0 minute (=0 hour), the level A (circle) is given for this status "HP".

As described above, according to this system, the vital data of the user can always be collected during the user's free ordinary life. In addition, the safety and health status of the user can be determined in association with its corresponding level, based on the total time of each status, thereby enabling to accurately understand the level of the safety and health status on a daily basis.

The DS controller 101 activates the safety and health status determining part 105 in order to execute a step 1108 to determine the status of safety SST, based on the plural levels of the safety and health status that are determined in the step 1107.

Figure 12:
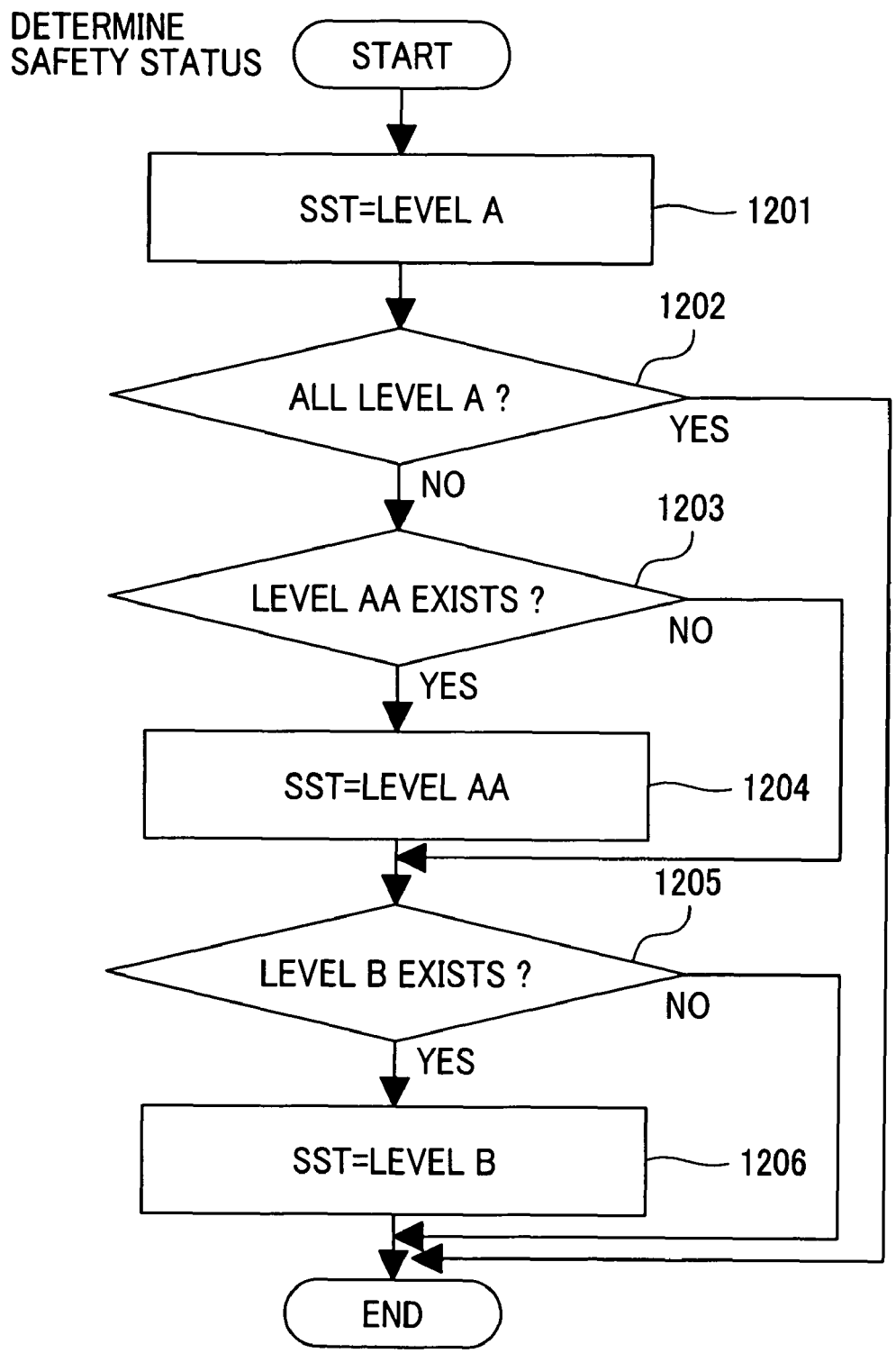
FIG. 12 is a flowchart for explaining operations of the data server at the time of determining the status of safety.

FIG. 12 shows a flowchart for explaining operations for determining the status of safety SST in the step 1108. For the initialization sake, the safety and health status determining part 105 executes a step 1201 to store "SST=level A" representing "the user is safe", in the DS memory 102. The safety and health status determining part 105 executes a step 1202 to determine whether "level A" is given for all of the determined safety and health statuses. If where "level A" is given for all of the determined statuses, this operation is ended.

In the step 1202, if it is determined that "level A" is not given for all of the determined safety and health statuses, the safety and health status determining part 105 executes a step 1203 to determine whether "level AA" is given for at least one of the determined safety and health statuses.

In the step 1203, if it is determined that "level AA" is not given for at least one of the determined safety and health status, the safety and health status determining part 105 executes a step 1205 to determine whether "level B" is given for at least one of the determined safety and health statuses.

In the step 1203, if it is determined "level AA" is given for at least one of the determined safety and health statuses, the safety and health status determining part 105 executes a step 1204 to store "SST=level AA" representing "the user is safe and healthy" in the DS memory 102, and continuously executes the step 1205.

In the step 1205, if it is determined that "level B" is not given for at least one of the safety and health statuses, the safety and health status determining part 105 ends this operation.

If it is determined that "level B" is given for at least one of the determined safety and health statuses in the step 1205, the safety and health status determining part 105 executes 1206 to store "SST=level B" representing "the user is not safe" in the DS memory 102, and ends this operation.

In this manner, corresponding levels are given for the plural the safety and health statuses, the status of safety can easily be determined.

The DS controller 101 activates the output part 106, and executes a step 1109 to create e-mail.

Figure 13:
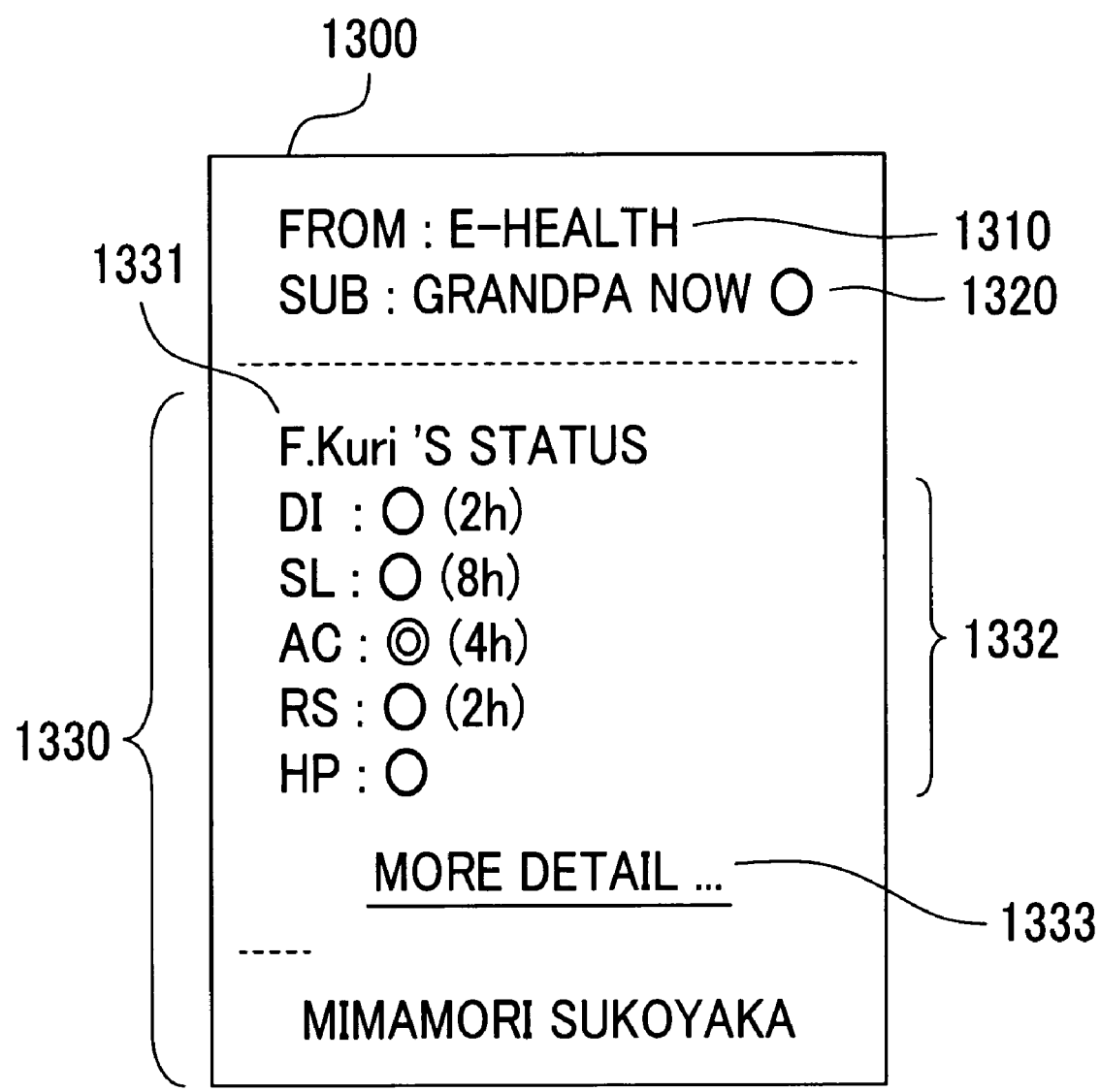
FIG. 13 is a diagram showing an example of created e-mail.

FIG. 13 shows an example 1300 of the e-mail created in the step 1109. The example 1300 includes data items of "from"

The "subject" 1320 shows text including the subject keyword stored in the field 226 of the family user information table 220, together with a mark (level A (circle), level AA (double circle) or level B (triangle)) representing the status of safety SST added to the subject keyword. The "text message" 1300 includes a user name 1331, a level of the safety and health status 1332 and a link 1333 for displaying a graphic image of the transition of the safety and health status.

The DS controller 101 activates the output part 106, and executes a step 1110 to send e-mail created in the step 1108. This transmission time is stored in the field 322 of the table 320.

The e-mail sent in the step 1110 is sent to the user terminal 190 through the provider 191.

Figure 14:
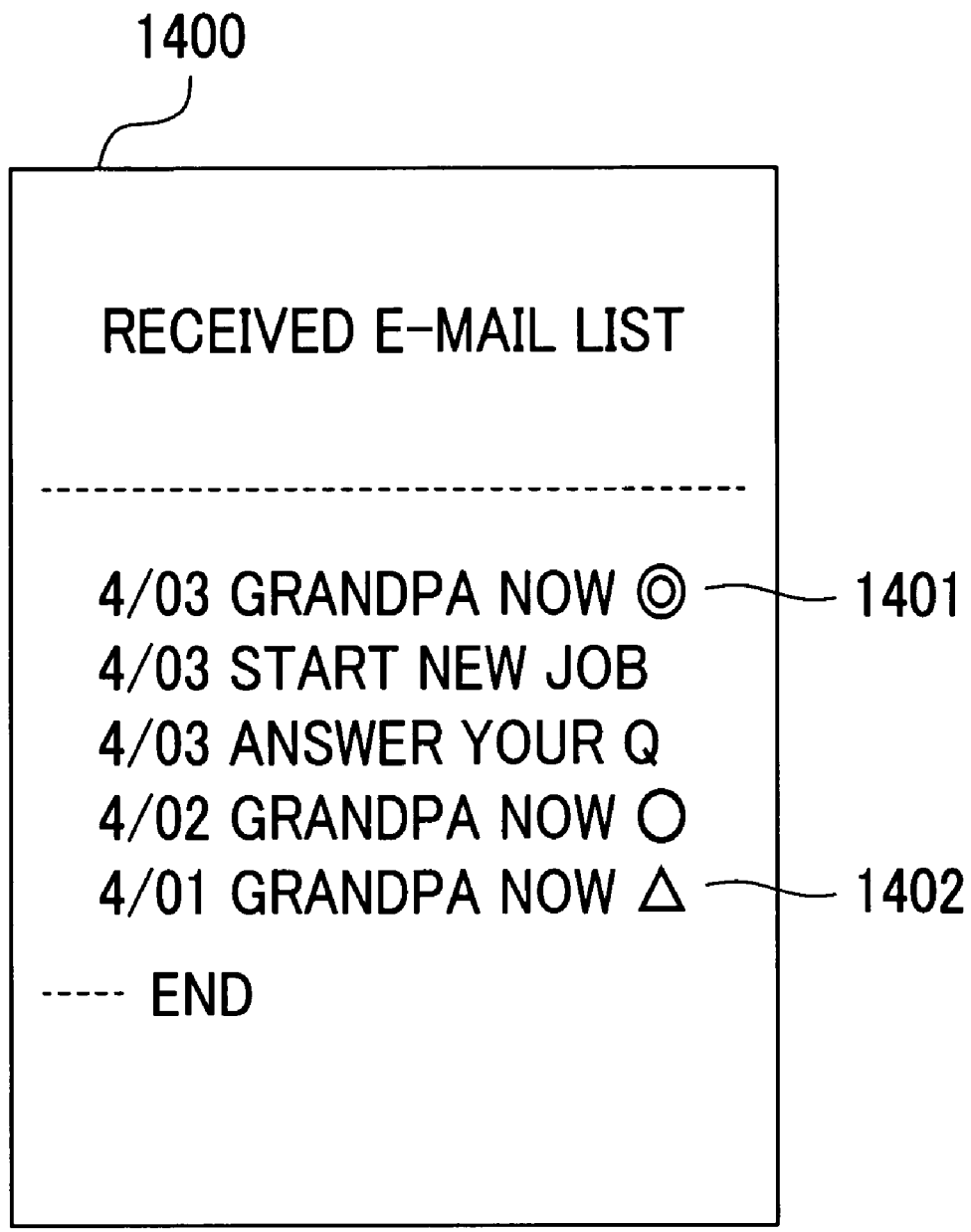
FIG. 14 is a diagram exemplifying a display screen shown on a user terminal at the time of displaying a list of e-mail.

FIG. 14 shows an example 1400 of a display screen when the e-mail sent in the step 1109 is received in the user terminal 190.

The screen example 1400 shows the subject of the e-mail sent in the Step 1109 together with the subjects of other e-mail, in the form of a list.

Because the subject shows the subject keyword set by the family user, the family user can immediately make sure whether the e-mail is the applicable mail sent from the system.

The subject is displayed so that the status of safety is clearly shown. Thus, the family user can immediately understand the status of safety of the user, and be assured of the user's status.

If the family user selects one of the subjects through the operation of the user terminal 190 displaying the screen example 1400, the display screen of the user terminal 190 shows the e-mail identified by the selected subject.

For example, if the family user selects the subject 1401, the e-mail of the example 1300 is displayed on the screen of the user terminal 190. Then, the family user can make sure the health status of the user and can feel relieved.

Because the display of the user terminal 190 shows the user name, the family user can soon make sure that the sent information is to report the resident.

If the family user selects the link 1333 displayed on the display of the user terminal 190, the user terminal 190 displays an image of the safety and health status in the form of a graphic image for showing the transition of the status.

Figure 16:
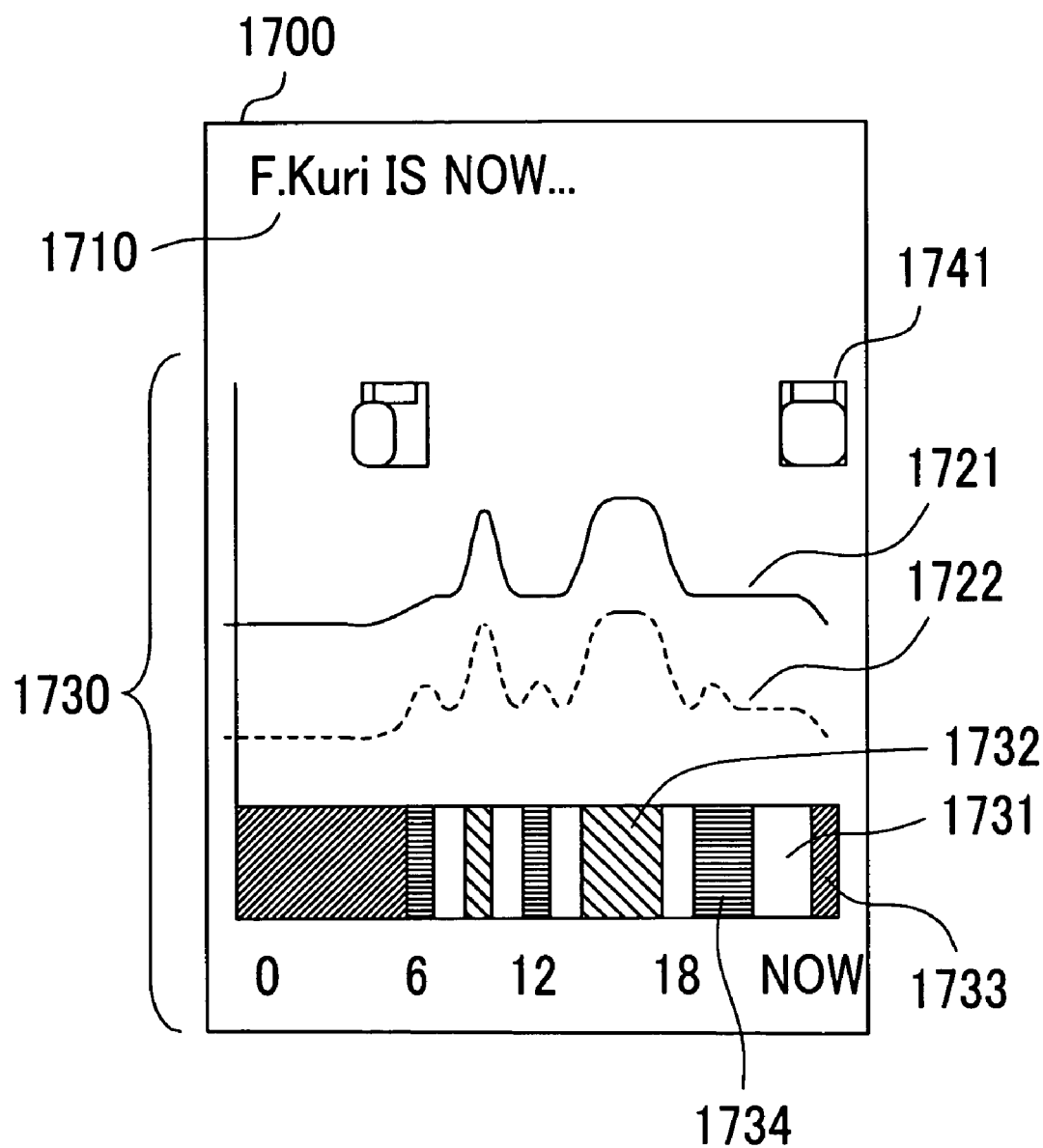
FIG. 16 is a diagram exemplifying a display screen shown on the user terminal at the time of displaying a graphic image of the transition in the safety and health status.

FIG. 16 shows a display image 1700 of the user terminal 190 that shows the image of the safety and health status. The display image 1700 includes a user name 1710, graphs 1730 showing the transition of the user data for the past twenty five hours by now and an image 1741 showing the user data detected by the placed device. The graphs 1730 include a time-series graph 1721 showing the transition of the activity index, a time-series graph 1722 showing the transition of the metabolic index, and bar graphs 1731, 1732, 1733 and 1734 showing the transition of the respective statuses "resting" (S_ST), "being active" (S_AC), "sleeping" (S_SL) and "dining" (S_DI).

With this display, the family user can make sure the safety and health status of the user in detail, and thus can be assured of the user's status.

Though not shown in the graphs 1730, any other status "health problem" (H_PN), "health problem(s)" (H_PS), or "health problem(e)" (H_PE) may be displayed. In this case, the family user can know that the user has a health problem.

The graphs 1730 may include only a limited number of user data items. By so doing, the simple display screen can be shown.

In this embodiment, when the safety and health status of the user just turns to "sleeping", the status of health and the status of safety can be reported to the family user on a daily basis. Thus, the family user who normally goes to bed after the user can make sure the safety and health status of the user before the day is over. In the case where the safety and health status of the user is not "safe", the family user can visit the user as soon as possible.

For example, if the family user selects a subject 1402 representing that the status of safety indicates the level B, the user terminal 190 displays a display example 1500 show in FIG. 15. From this illustration, it is apparent that the triangle (level B) is given for the safety and health status "being active" (AC) 1532. In this way, the families who watch the user can immediately make sure the reason why the user is not safe. Even if the status of safety of the user represents "not safe", the family user may at least give a sigh of relief by knowing the condition of the user.

Back to FIG. 10, the DS controller 101 executes the step 1007 to determine whether the safety and health status obtained in the step 1004 is "health problem in emergency" (H_PE), after execution of the step 1006. If the DS controller 101 determines in the step 1007 that the obtained status is not "health problem in emergency" (H_PE), it executes the step 1001, and repeats the following operations.

If it is determined in the step 1007 that the status is "health problem in emergency" (H_PE), the DS controller 101 activates the output part 106 in order to execute a step 1008 to report the status of the user to the customer center by phone or by alarm and to create urgent e-mail for reporting.

Figure 17:
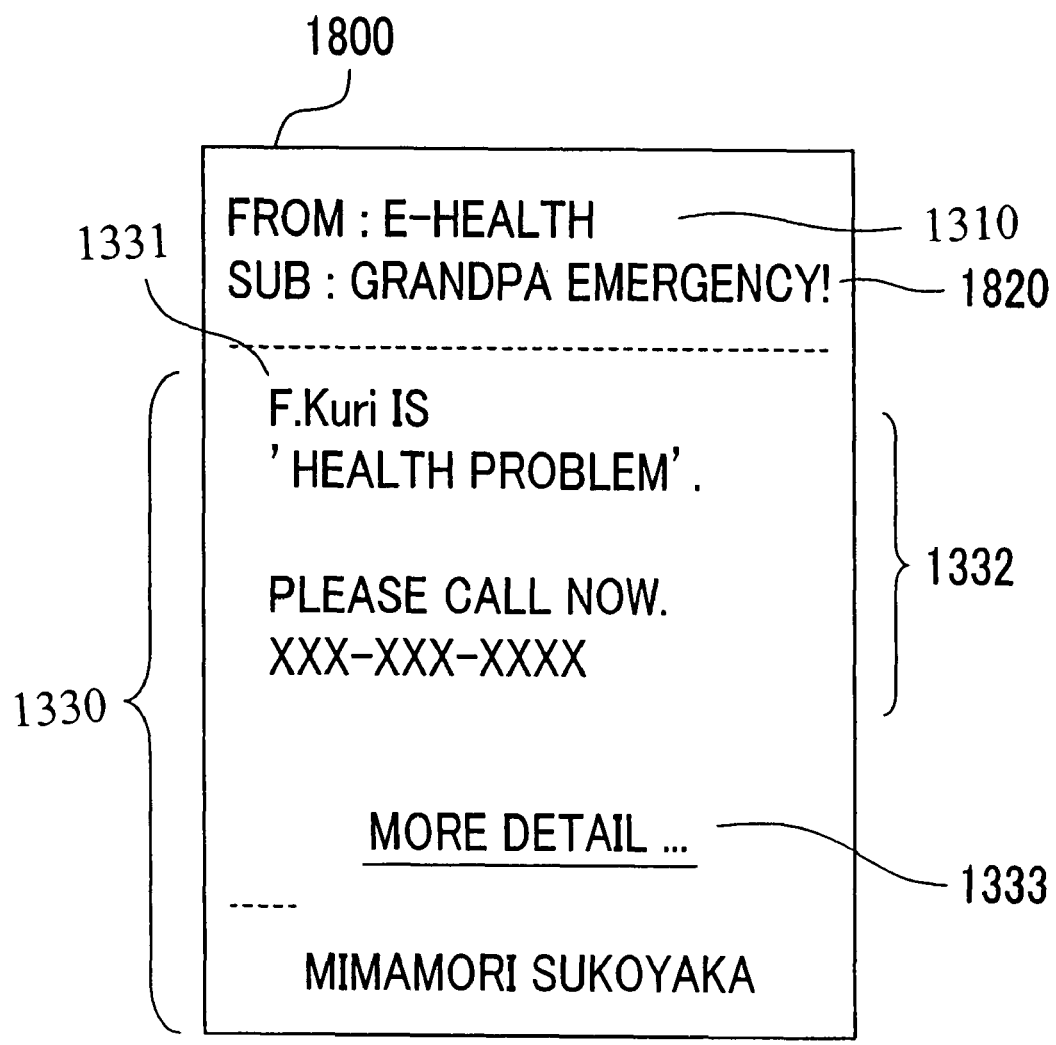
FIG. 17 is a diagram exemplifying a display screen shown on the user terminal at the time of displaying e-mail in an emergency.

FIG. 17 shows an example 1800 of the urgent e-mail created in the step 1008. Like the example 1300, a subject 1820 shows text including a subject keyword stored in the field 226 of the family user information table 220, together with "emergency" representing that the user has some health problem in emergency.

If it is determined that the safety and health status of "health problem in emergency" (H_PE) (i.e. the user is not safe and must have a problem), the system immediately reports this status. Thus, the family user can soon be aware of the problem of the user.

According to the above-described safety and health information reporting system, because the family user can easily know the safety and health status of the user in detail, the family user can be assured and remotely watch the user.

Because the user is aware of the fact that his/her families watch the user, the user can lead a comfortable daily life without anxiety.

If the human detection sensor 166 of the placed device 150 is a piezoelectric sensor, it statistically processes the voltage value output by the piezoelectric sensor, thereby detecting the heart rate HR (pulse Ps) (i.e. the pulsation of the heart of the living body) and the vital data Ac (e.g. body movement). If the human detection sensor 166 is a pyroelectric infrared sensor, the body temperature BT can be detected using a transformation for transforming the voltage value output from the pyroelectric infrared sensor into a temperature.

As described above, the human detection sensor 166 of the placed device 150 is formed in combination with the piezoelectric sensor and the pyroelectric infrared sensor. As a result, if the user is not wearing the wearable device, for example, if the placed device 150 is installed in the bed and the user takes off the wearable device before going to bed, the safety and health status of the user can be determined based on the heart rate HR, the body movement Ac and the body temperature BT output by the wearable device 150, just like the user is wearing the wearable device.

What is claimed is:

1. A safety and health information reporting system comprising:
a wearable device having a pulse wave sensor, a temperature sensor and a movement sensor, and which is worn by a living body;
a metabolic index calculating part which calculates a metabolic index MtI representing a characteristic of a metabolism of the living body, based on a detected signal from the pulse wave sensor and the temperature sensor which detect a status inside of the living body;
an activity index calculating part which calculates an activity index AcI representing a characteristic of an activity amount of the living body, based on a detected signal from the movement sensor which detect a status of a movement of the living body;
a safety and health status determining part which determines a safety and health status of the living body, wherein the safety and health status determining part determines the safety and health status by comparing the metabolic index MtI calculated by the metabolic index calculating part and the activity index AcI calculated by the activity index calculating part, with respective predetermined index values; and
a determination result output part which outputs the determination result from the safety and health status determining part,
wherein the safety and health status includes a living condition normal daily factor and health problem information, and
wherein the safety and health status determining part determines:
a period of sleeping which is calculated based on a start time of sleeping and an end time of sleeping;
a period of being active from the end time of sleeping to the start time of sleeping;
a period of resting from the end time of sleeping to the start time of sleeping;
a period of dining from the end time of sleeping to the start time of sleeping; and
whether a heath problem is found.

2. The safety and health information reporting system according to claim 1, wherein the metabolic index calculating part is configured to calculate the metabolic index, based on an output signal of the pulse wave sensor and an output signal of the temperature sensor.

3. The safety and health information reporting system according to claim 1, wherein the activity index calculating part is configured to calculate the activity index based on an output signal of the movement sensor.

4. The safety and health information reporting system according to claim 1, wherein the determination result output part outputs a determination result of the safety and health status determining part when the safety and health status determining part determines that the living body is in a state of sleeping.

5. The safety and health information reporting system according to claim 1, wherein the determination result output part outputs a determination result of the safety and health status determining part via an e-mail.

6. The safety and health information reporting system according to claim 1, wherein the determination result output part generates a graph including the activity index, the metabolic index and the determination result, and outputs the generated graph.

7. The safety and health information reporting system according to claim 1, further comprising
a placed device including a human detection sensor which detects the living body, wherein
the safety and health status determining part outputs information representing a health problem of the living body, based on a detection signal of the human detection sensor.

8. The safety and health information reporting system according to claim 1, wherein the safety and health status determining part outputs e-mail representing that the health problem is determined upon determination of the health problem.

9. The safety and health information reporting system according to claim 1, wherein
a safety and health status determining part is further configured to determine the health problem of the living body based on one of predetermined health problem conditions H_PN, H_PS and H_PE, and
the safety and health status determining part further determines the health problem based on:
$AcI < AcI\_L$ and $MtI > MtI\_H$ indicating the health problem condition H_PN,
$AcI > AcI\_H$ and $MtI < MtI\_L$ indicating the health problem condition H_PS, and
$AcI < AcI\_LL$ and $MtI < MtI\_LL$ indicating the health problem condition H_PE.

10. A safety and health information reporting system comprising:
a wearable device having a pulse wave sensor, a temperature sensor and a movement sensor, and which is worn by a living body;
a metabolic index calculating part which calculates a metabolic index MtI representing a characteristic of a metabolism of the living body, based on a detected signal from the pulse wave sensor and the temperature sensor which detect a status inside of the living body;
an activity index calculating part which calculates an activity index AcI representing a characteristic of an activity amount of the living body, based on a detected signal from the movement sensor which detect a status of a movement of the living body;
a safety and health status determining part which determines a safety and health status of the living body, wherein the safety and health status determining part determines the safety and health status by comparing the metabolic index MtI calculated by the metabolic index calculating part and the activity index AcI calculated by the activity index calculating part, with respective predetermined index values; and
a determination result output part which outputs the determination result from the safety and health status determining part,
wherein the safety and health status includes a normal daily factor and health problem information, and
the safety and health status determining part determines a status of safety of the living body as to whether the living body is in a usual status or not.

11. The safety and health information reporting system according to claim 10, wherein the determination result output part writes the status of safety of the living body in a subject of the email.

12. A safety and health information reporting system according to claim 10, wherein the determination result output part reports the unusual status when the safety and health status is determined to be an emergency health problem.

* * * * *